(12) United States Patent
Vilendrer

(10) Patent No.: US 12,306,018 B1
(45) Date of Patent: May 20, 2025

(54) MATERIAL TESTING APPARATUS HAVING VIBRATION MITIGATION

(71) Applicant: ST3 Development Corporation, Eden Prairie, MN (US)

(72) Inventor: Kent Vilendrer, Eden Prairie, MN (US)

( * ) Notice: Subject to any disclaimer, the term of this patent is extended or adjusted under 35 U.S.C. 154(b) by 380 days.

(21) Appl. No.: 17/992,593

(22) Filed: Nov. 22, 2022

(51) Int. Cl.
| | |
|---|---|
| *G01D 11/14* | (2006.01) |
| *G01B 7/24* | (2006.01) |
| *G01N 3/38* | (2006.01) |
| *G01N 33/483* | (2006.01) |

(52) U.S. Cl.
CPC ............. *G01D 11/14* (2013.01); *G01B 7/24* (2013.01); *G01N 3/38* (2013.01); *G01N 33/4833* (2013.01); *G01N 2203/0005* (2013.01); *G01N 2203/0019* (2013.01)

(58) Field of Classification Search
CPC .......... G01D 11/10; G01D 11/14; G01B 7/16; G01B 7/24; G01N 33/4833; G01N 3/38; G01N 2203/0005; G01N 2203/0007; G01N 2203/0016; G01N 2203/0017; G01N 2203/0019
See application file for complete search history.

(56) References Cited

U.S. PATENT DOCUMENTS

| | | |
|---|---|---|
| 3,277,555 A | 10/1966 | Kutash |
| 3,789,508 A | 2/1974 | Meline |
| 5,216,723 A | 6/1993 | Froeschle et al. |
| 5,370,457 A * | 12/1994 | Iizuka .................. G01N 3/38 73/818 |
| 5,670,708 A * | 9/1997 | Vilendrer ............. G01N 3/12 73/37 |
| 5,712,431 A | 6/1998 | Vilendrer |
| 5,767,402 A | 6/1998 | Sandlass et al. |
| 6,405,599 B1 | 6/2002 | Patt |
| 6,598,486 B2 | 7/2003 | Vilendrer et al. |
| 7,252,053 B2 | 8/2007 | Froeschle et al. |
| 7,679,229 B2 | 3/2010 | Mark |
| 7,694,593 B2 | 4/2010 | Owens et al. |
| 8,610,318 B2 | 12/2013 | Oommen et al. |
| 9,410,113 B2 | 8/2016 | Vilendrer et al. |
| 9,601,969 B2 * | 3/2017 | Lucas .................. H02K 1/34 |
| 10,028,062 B2 * | 7/2018 | Lucas .................. H04R 11/02 |

(Continued)

FOREIGN PATENT DOCUMENTS

| | | | | |
|---|---|---|---|---|
| CH | 644450 A5 * | 7/1984 | | |
| CN | 112881172 A * | 6/2021 | ........... | G01N 3/02 |

OTHER PUBLICATIONS

Machine Translation of CH 644450 (Year: 1984).*
Machine Translation of CN 112881172 (Year: 2021).*

*Primary Examiner* — Nathaniel J Kolb
(74) *Attorney, Agent, or Firm* — Dietz Law Office LLC

(57) ABSTRACT

A material testing apparatus of the present invention may be used as a stand-alone tester coupled to a single environmental chamber. Alternatively, a plurality of material testing apparatus of the present invention may be coupled to a common frame to form a multi-station material testing system. The material testing apparatus of the present invention includes a linear actuator that provides a repetitive linear load or displacement on an object or specimen while canceling vibrations caused by actuation of the linear actuator.

24 Claims, 37 Drawing Sheets

(56) References Cited

U.S. PATENT DOCUMENTS

2005/0153436 A1* 7/2005 Vilendrer ............... C12M 35/04
                                                    435/289.1
2010/0255582 A1* 10/2010 Porter .................. C12N 5/0068
                                                    435/297.1

* cited by examiner

MATERIAL TESTING APPARATUS HAVING VIBRATION MITIGATION

CROSS-REFERENCE TO RELATED APPLICATIONS

Not Applicable

FEDERAL SPONSORSHIP

Not Applicable

JOINT RESEARCH AGREEMENT

Not Applicable

TECHNICAL FIELD

This invention pertains generally to material testing systems. More particularly, the invention pertains to a material testing apparatus capable of controlling either a repetitive linear load or displacement on a specimen. The material testing apparatus of the present invention has a unique linear actuator that delivers a linear force or displacement. The linear actuator of the present invention includes a plurality of armatures and flexures that cancel vibration caused by actuation of the linear actuator while providing an additive linear actuation force. This invention further pertains to a material testing apparatus that can be quickly altered from use as standalone single station tester to a combination multi apparatus to form a larger multi-station assembly.

BACKGROUND

Generally, research and development of components or materials in many fields and disciplines require testing before the component or material is adopted or incorporated into a product. Linear motors or actuators have been proven effective in applying a repetitive linear force (load) or displacement to a sample material or component being tested. By way of example, systems applying a linear load or displacement to a sample may impart fatigue or wear, and may be used to determine the elasticity, endurance, durability, or longevity of the sample. Alternatively, the test system may utilize a linear load or displacement (push or pull) to condition a material or specimen. Linear actuators are particularly useful in other fields as well, however, the motion of the linear actuator tends to create an added undesirable vibration that may translate to the object or sample being actuated or to the instrumentation being used to measure the applied load to the specimen. Further, these vibrations and induced accelerations may skew test results or may require additional components to compensate for or dampen the undesirable vibration. Additionally, the vibrations may transmit to surrounding test instruments, positioned on the same test bench or mounted to a common framework, further skewing test results. Thus, a linear actuator and test system that cancels its own vibrations is desirable.

SUMMARY

Embodiments according to aspects of the invention include a material testing apparatus having vibration mitigation. Further, in accordance with aspects of the invention a linear actuator of the present invention is implemented into the material testing apparatus to deliver an increased actuating force while reducing vibration. Particular embodiments of the material testing apparatus include a frame or support framework, a linear actuator, a linear displacement assembly, a displaceable base, and a displacement flexure interconnecting the linear actuator with the displacement assembly and a load sensing assembly. The frame or support framework is comprised of a combination of components and panels thereby eliminating the need for a separate rigid core.

The linear actuator includes a stator coupled to the frame and first and second armatures pivotally mounted to the frame. A transfer flexure transfers the linear force from the armatures to the displacement assembly. The first armature includes a cross-flexure assembly, arms and a first set of permanent magnets. The arms interconnect the cross-flexure assembly and the first set of permanent magnets. A first end of the arms of the first armature are coupled to the cross-flexure assembly and a free end of the arms of the first armature has the first set of permanent magnets affixed thereto. The magnets move within a gap of the stator and frames of the magnets are connected to the linear displacement assembly via the transfer flexure. Those skilled in the art will appreciate that the linear displacement assembly may simply include structure to couple the armatures to a specimen or alternatively may include load or displacement sensing capability incorporated into the linear displacement assembly. A portion of the cross-flexure assembly is fixed to the frame and another portion of the cross-flexure assembly is mounted to the arms of the first armature to allow the arms to pivot.

Similarly, the second armature includes a cross-flexure assembly, arms and a first set of permanent magnets. The arms interconnect the cross-flexure assembly with the second set of permanent magnets. A first end of the arms of the second armature are coupled to the cross-flexure assembly. A free end of the arms of the second armature has the second set of permanent magnets affixed to the free end. The magnets move within a gap of the stator. A portion of the cross-flexure assembly is fixed to the frame and another portion of the cross-flexure assembly is mounted to the arms of the second armature to allow the arms to pivot. An interconnecting flexure connects the pivoting end of the cross-flexure assembly of the first armature with the pivoting end of the cross-flexure assembly of the second armature.

In accordance with aspects of the invention the stator includes first and second spaced apart c-shaped cores oriented such that ends of the first and second c-shaped cores are aligned but opposed to form a first gap and a second gap between opposing ends of the first and second c-shaped cores. Each end of each of the first and second c-shaped cores includes a coil surrounding the end. The first set of permanent magnets are positioned within the first gap and the second set of permanent magnets are positioned in the second gap. Applying a current through the coils is controlled by a micro controller. Current flowing through the coil creates a magnetic field that repels the permanent magnets causing the free end of the arms of each armature to move in an arc that is centered on the cross-flexure assembly. The arced motion of the first set of permanent magnets is connected to the linear load displacement assembly via the transfer flexure. The linear load displacement assembly moves in a linear motion along a single axis.

The cross-flexure assembly of the first or lower armature includes two flexures and each of the two flexures includes one or more strain gages coupled thereto. The cross-flexure assembly of the second or upper armature includes two flexures that do not require strain gages. A micro controller, an integrated circuit and associated components control and monitor actuation of the linear actuator and linear displacement of the linear displacement assembly. The linear displacement assembly may additionally include a displacement sensor controlled by the micro controller. The portion of the cross-flexure assembly of the first armature that is fixed to the frame is spaced apart along the load axis from the portion of the cross-flexure assembly of the second armature that is fixed to the frame. The first and second armatures have the same mass and the free end of the arms of the first armature and the free end of the arms of the second armature move or pivot in opposing directions. The movement in opposing directions cancels vibrations from movement of the first and second armatures along the loading axis. Specifically, movement of the armatures with equal and opposite motion from accelerations of the two magnet assemblies effectively cancel out opposing vibrations. To provide additional vibration cancellation, for the mass of the displacement assembly and test specimen, additional mass may be added to the upper armatures. Further, movement of the first and second armatures provides an additive force against the linear displacement assembly. In certain further aspects of the invention a framework is provided that is suitable for coupling a plurality of the apparatus in series, parallel, or in a horizontal arrangement.

In use, the material testing apparatus includes a test specimen. One end of the specimen is coupled to the linear displacement assembly. The other end of the specimen is coupled to a lower load cell to provide output related to the load applied to the specimen. When the linear actuator is activated, a repetitive, controlled load or force is applied to the specimen. The controller monitors the cycles and force or displacement applied to the specimen.

An environmental chamber with the specimen contained therein may be mounted to the displaceable base of the material testing apparatus. The environmental chamber may include a liquid or gas dependent upon the test being performed on the specimen contained within the chamber. For most medical device testing applications, the liquid is phosphate buffered saline (PBS). When the environmental chamber is used, the load cell is often mounted above the chamber to avoid submersing the load cell into the PBS solution. An internal loading frame transfers the linear actuator motion to the bottom of the test specimen while the top of the specimen is coupled to the load cell for load monitoring and control. Those skilled in the art will recognize that the load cell could be immersible and mounted within the chamber or below the chamber using a pull rod assembly with sealing arrangement. When the linear actuator is activated, a repetitive, controlled load or force is applied to the specimen. The controller monitors the cycles and force applied to the specimen. When multiple material testing apparatus are coupled to a framework, the controller may monitor the cycles and force applied to multiple specimens.

The accompanying drawings, which are incorporated in and constitute a portion of this specification, illustrate embodiments of the invention and, together with the detailed description, serve to further explain the invention. The embodiments illustrated herein are presently preferred; however, it should be understood, that the invention is not limited to the precise arrangements and instrumentalities shown. For a fuller understanding of the nature and advantages of the invention, reference should be made to the detailed description in conjunction with the accompanying drawings.

DESCRIPTION OF THE DRAWINGS

In the various figures, which are not necessarily drawn to scale, like numerals throughout the figures identify substantially similar components.

DETAILED DESCRIPTION

Figure 1:
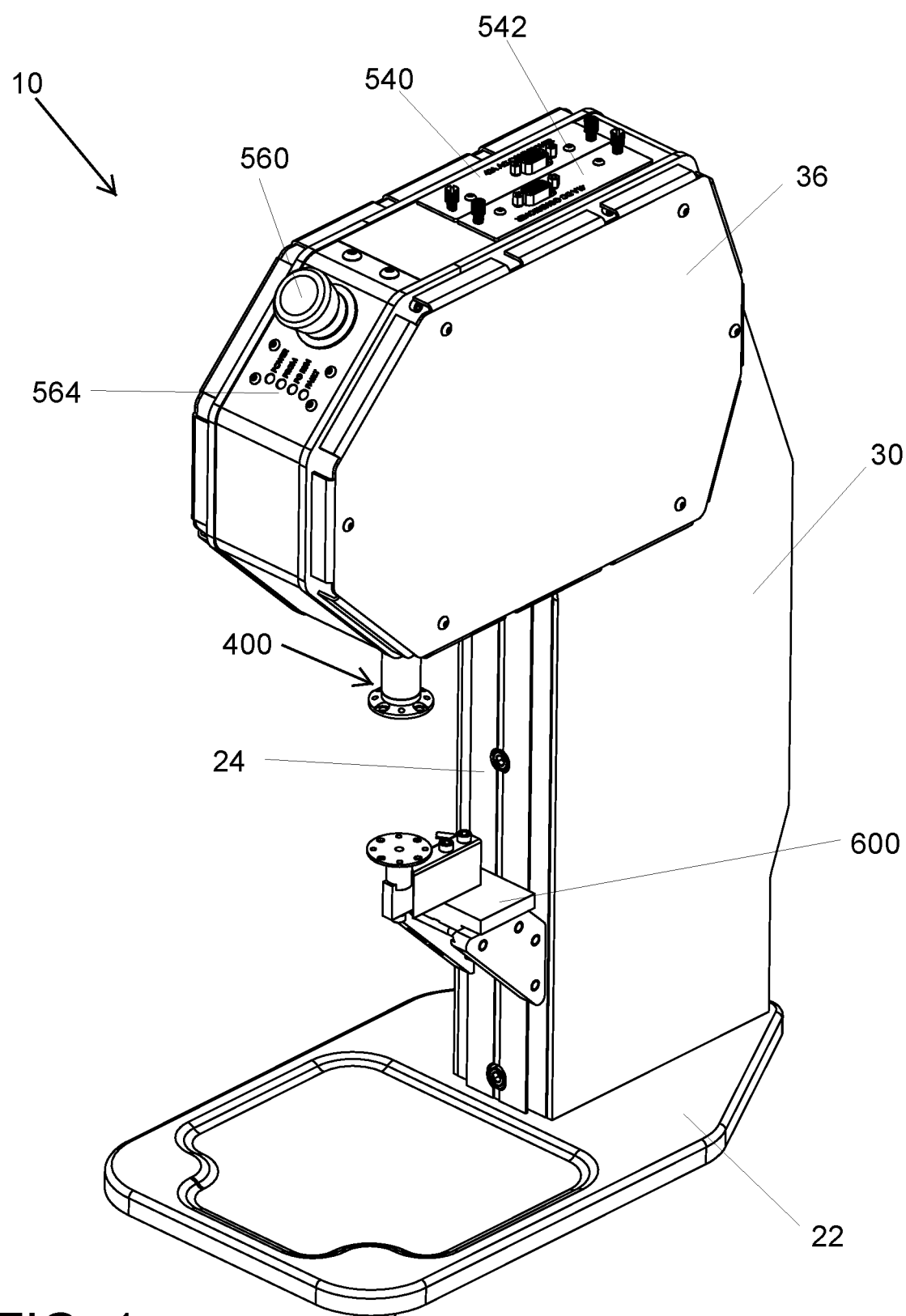
FIG. 1 is a front right top perspective view of a material testing apparatus in accordance with the present invention.
Figure 2:
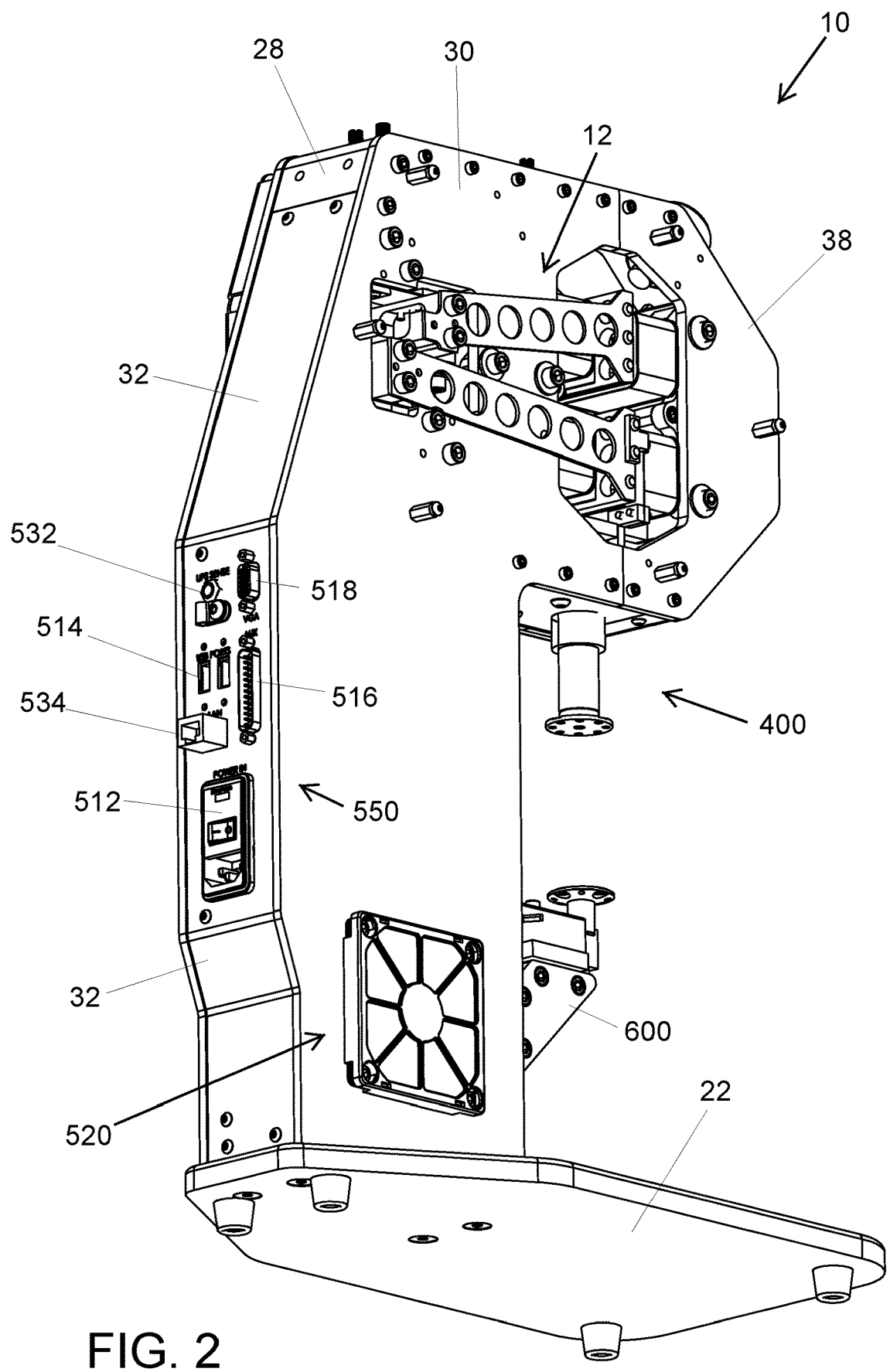
FIG. 2 is a back left bottom perspective view of a material testing apparatus in accordance with the present invention.

The following description provides detail of various embodiments of the invention, one or more examples of which are set forth below. Each of these embodiments are provided by way of explanation of the invention, and not intended to be a limitation of the invention. Further, those skilled in the art will appreciate that various modifications and variations may be made in the present invention without departing from the scope or spirit of the invention. By way of example, those skilled in the art will recognize that features illustrated or described as part of one embodiment, may be used in another embodiment to yield a still further embodiment. Thus, it is intended that the present invention also cover such modifications and variations that come within the scope of the appended claims and their equivalents.

The apparatus of the present invention is particularly well suited for medical device testing. It is also particularly well suited for tissue cell testing, conditioning, and growth. The material testing apparatus 10 of the present invention generally includes a framework, a linear actuator 12, linear displacement assembly 400, a load sensing assembly 600, an environmental chamber 450, and a controller 500. Although an internal framework could be utilized without departing from the scope of the invention, rather than requiring a single unitary core frame or internal frames, the framework is created or formed from the fixation or coupling of several components to external side plates. In this manner, the apparatus includes a framework without requiring a separate dedicated frame. The linear actuator 12 of the present invention includes an upper armature 100 and lower armature 200 that cooperate with two c-shaped stators 50 in conjunction with cross-flexure assemblies 150 and 250 to deliver a load or displacement to the linear displacement assembly 400. The lower armature 200 is coupled to the linear displacement assembly 400. The linear displacement assembly 400 may be coupled directly to a testing sample or may be coupled to a secondary frame within an environmental chamber 450 that contains the testing sample within the chamber. The other end of the test specimen is coupled to the load sensing assembly 600 so that the applied force to the specimen can be measured. The various features of the invention will be described in conjunction with the Figures.

With reference to the Figures, various embodiments according to aspects of the invention will be described in greater detail. With reference first to FIGS. 1-8, the material testing apparatus 10 is generally comprised of a support framework, a linear actuator 12, a linear displacement assembly 400, load sensing assembly 600, and electronic based components including a micro controller 500. The support framework includes a base 22, column 24, rear side plates 30, top plates 40, front shroud 42, back shroud 32, side covers 36, front side plates 38, and linear bushing plate 360. The plates are made of a material having a sufficient gauge or thickness to vertically support the components attached thereto. Displaceable base 44 features a dovetail that couples to column 24, allowing the displaceable base 44 to slide up or down vertically. The displaceable base further includes a mount 45 that interfaces with the displaceable base to support a lower load cell 48. The mount enables the load cell to be positioned inward and outward for alignment. The load cell sensing end is connected to the lower grip attachment point 406. When combined with lower grip attachment point, the load cells used in this application typically have a very low critical damping ratio (approximately 0.03) and, as a result, may overstate the applied load at accelerated test frequencies. For this reason, mount 45 includes a pocket that is positioned beneath the lower grip attachment point 406. A damper 43 is placed in the pocket and makes contact with the attachment point screw to increase the load cell/grip attachment point damping ratio. The damper can either be made from viscoelastic material or can be a viscous fluid.

Figure 3:
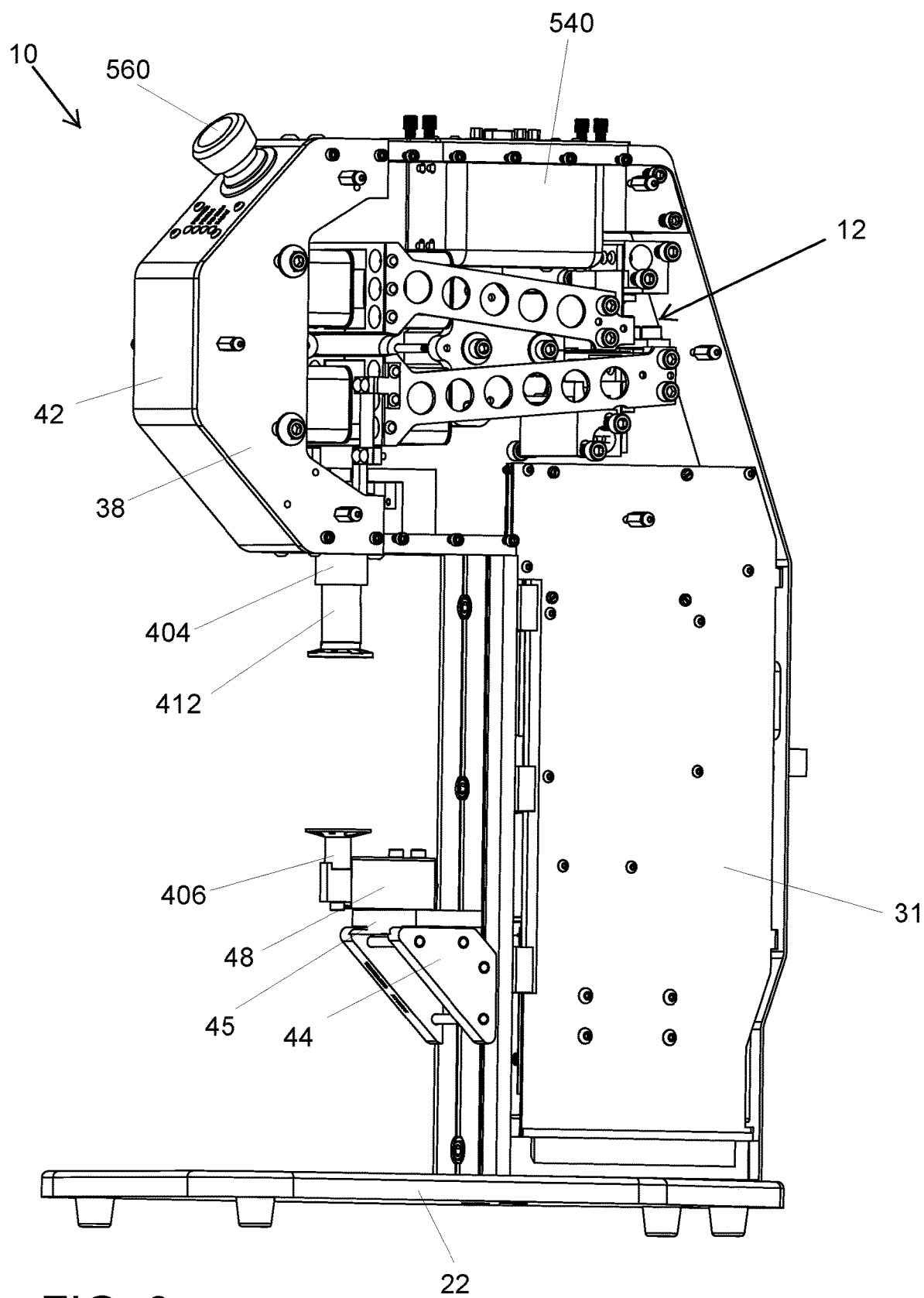
FIG. 3 is a right side perspective view of the material testing apparatus in accordance with the present invention and illustrating the right rear side plate and right side cover removed.
Figure 4:
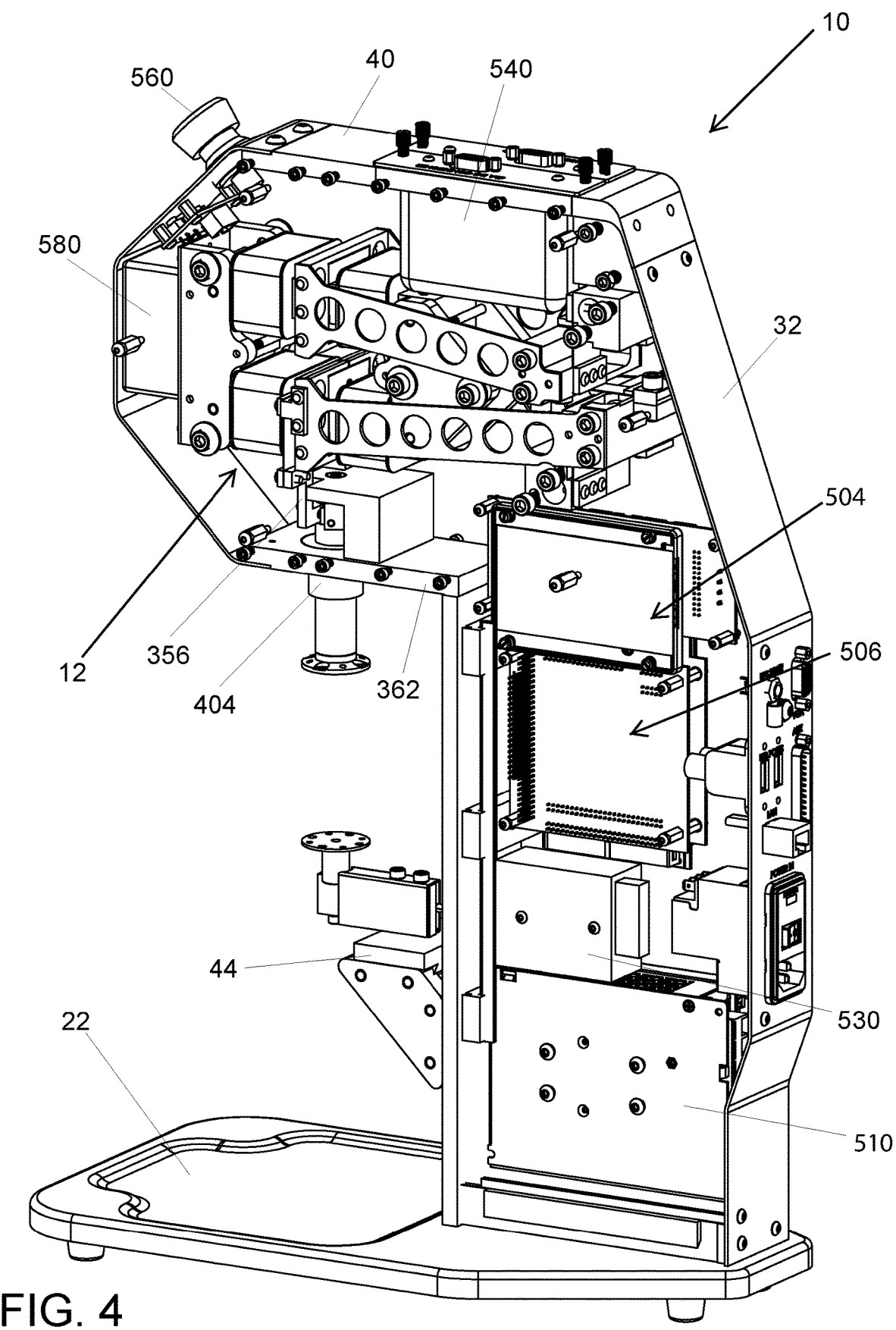
FIG. 4 is a right side perspective view of the material testing apparatus in accordance with the present invention and illustrating the right front and rear side plates and side cover removed.
Figure 5:
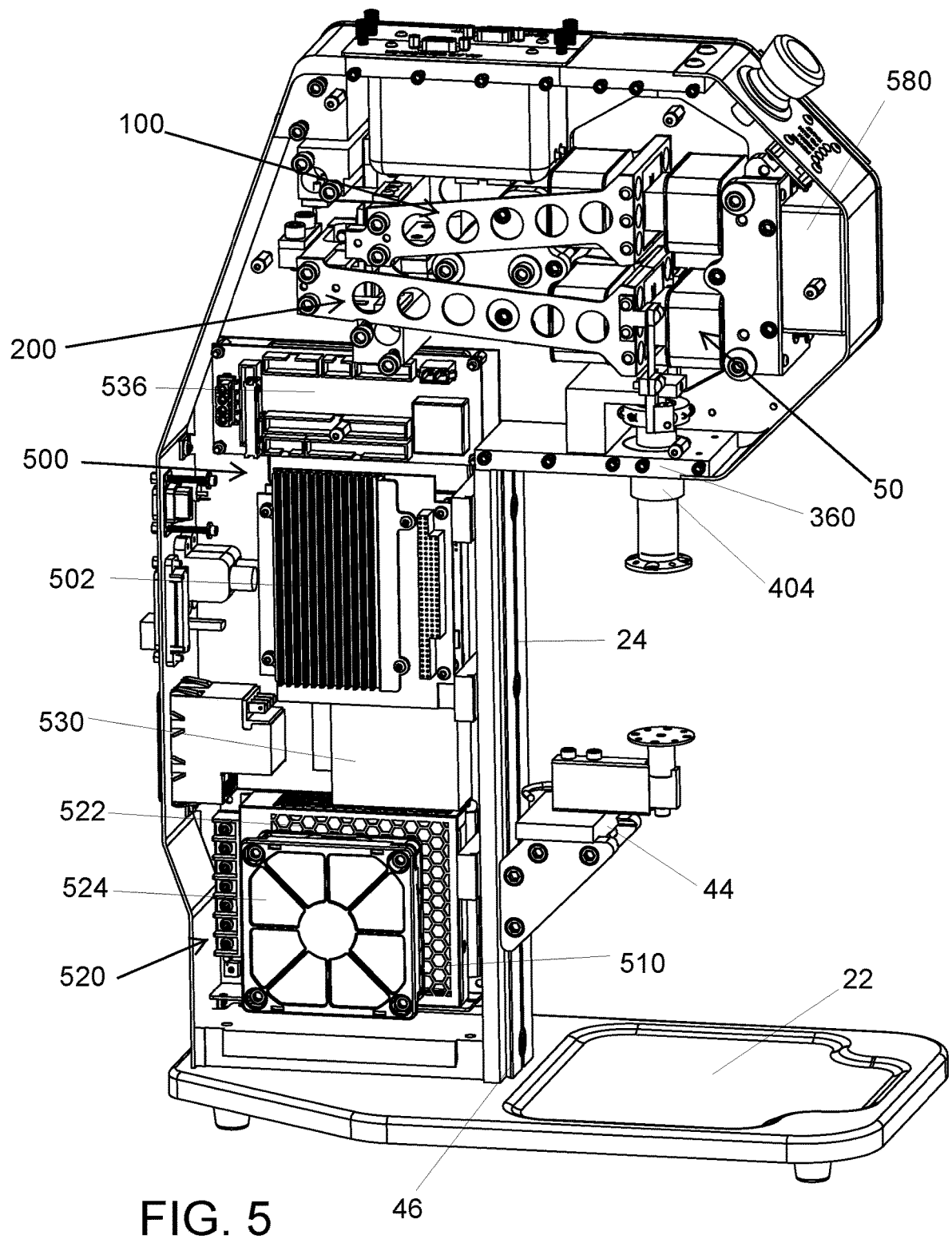
FIG. 5 is a left side perspective view of the material testing apparatus in accordance with the present invention and illustrating the left front and rear side plates and left side cover removed.
Figure 6:
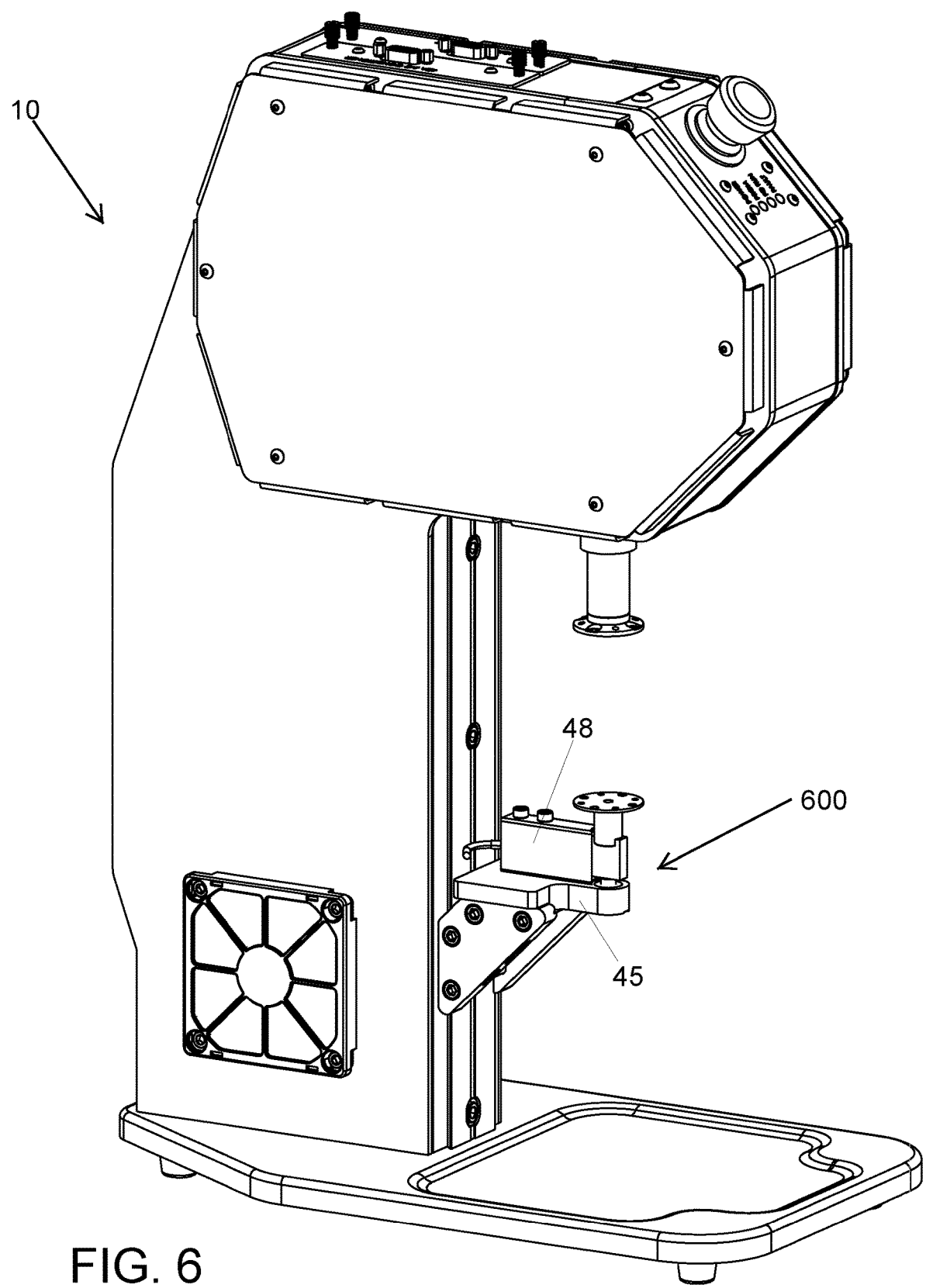
FIG. 6 is a left perspective view of a material testing apparatus in accordance with aspects of the present invention
Figure 7:
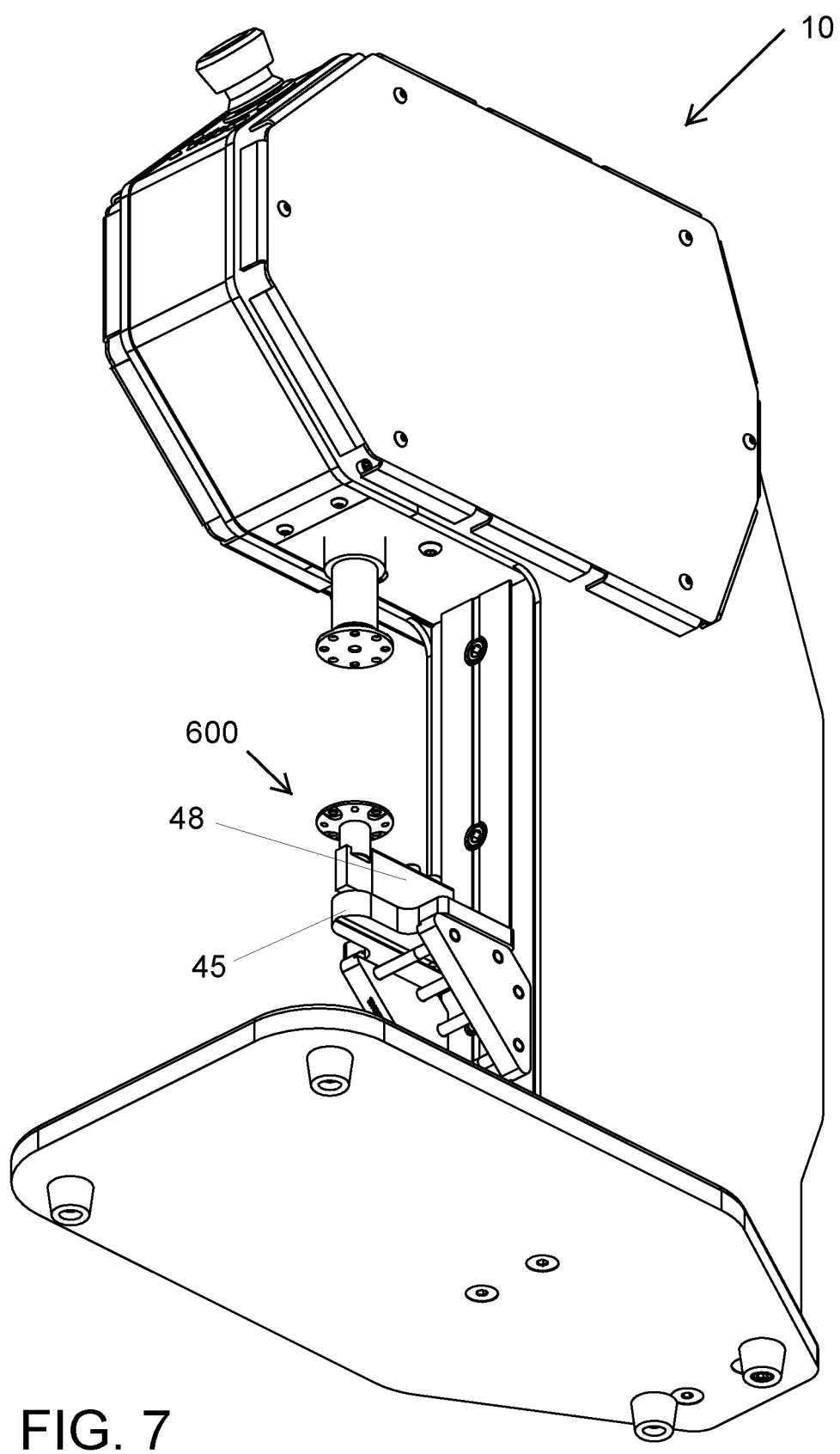
FIG. 7 is a right bottom perspective view of the material testing apparatus of the type shown in FIG. 6.
Figure 8:
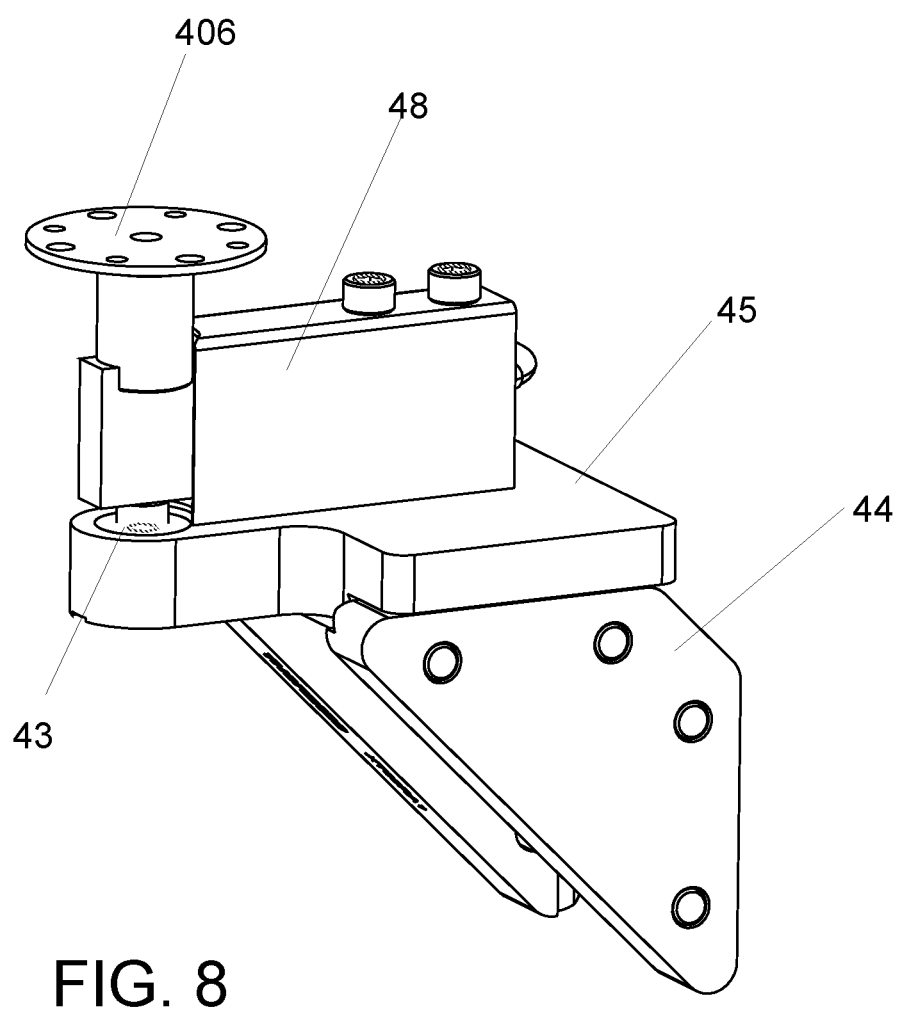
FIG. 8 is a perspective view of a load assembly of an embodiment of the material testing apparatus in accordance with the present invention.
Figure 9:
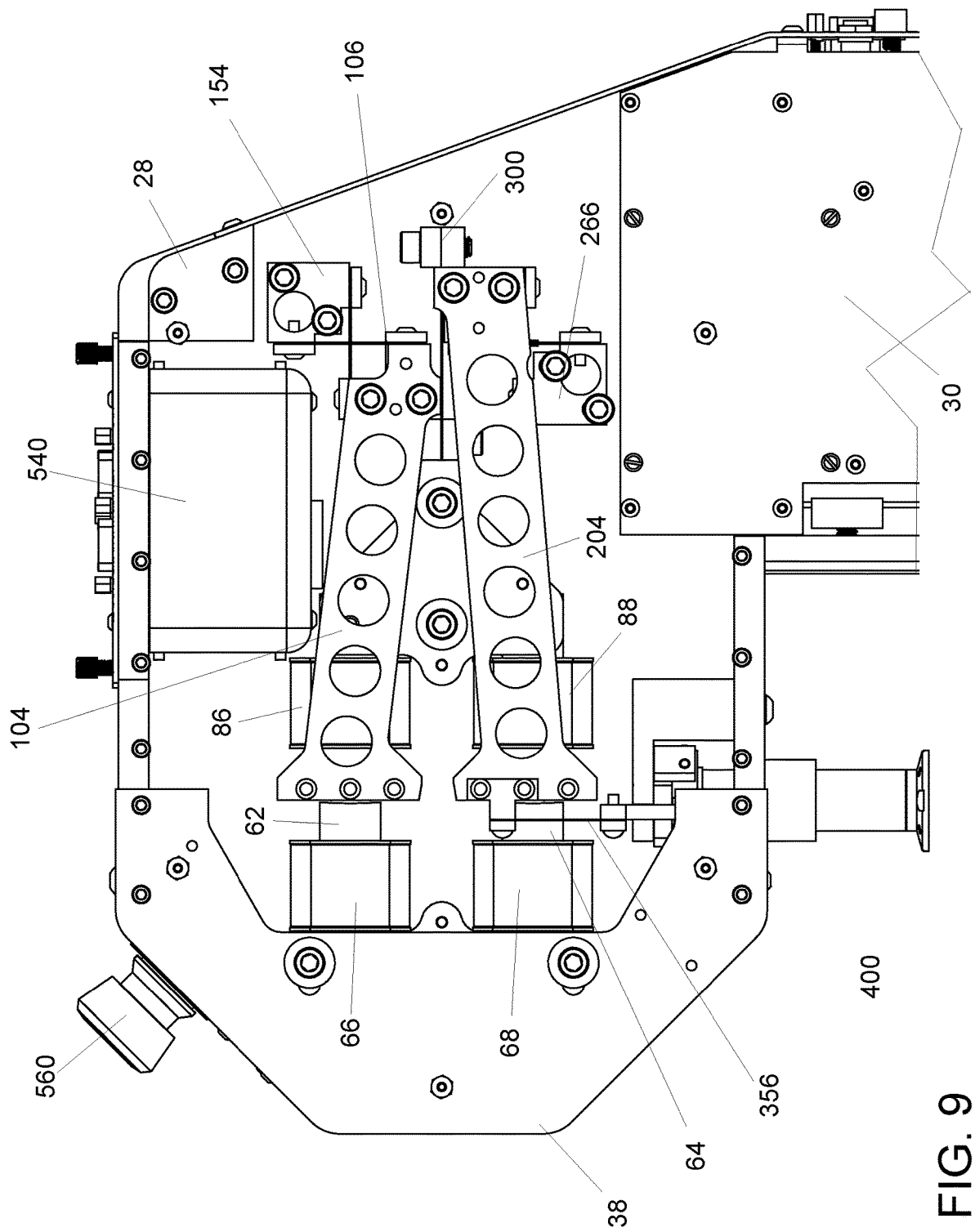
FIG. 9 is a partial sectional right perspective view of the upper portion of the material testing apparatus in accordance with the present invention and illustrating the right rear side plates and side cover removed.
Figure 10:
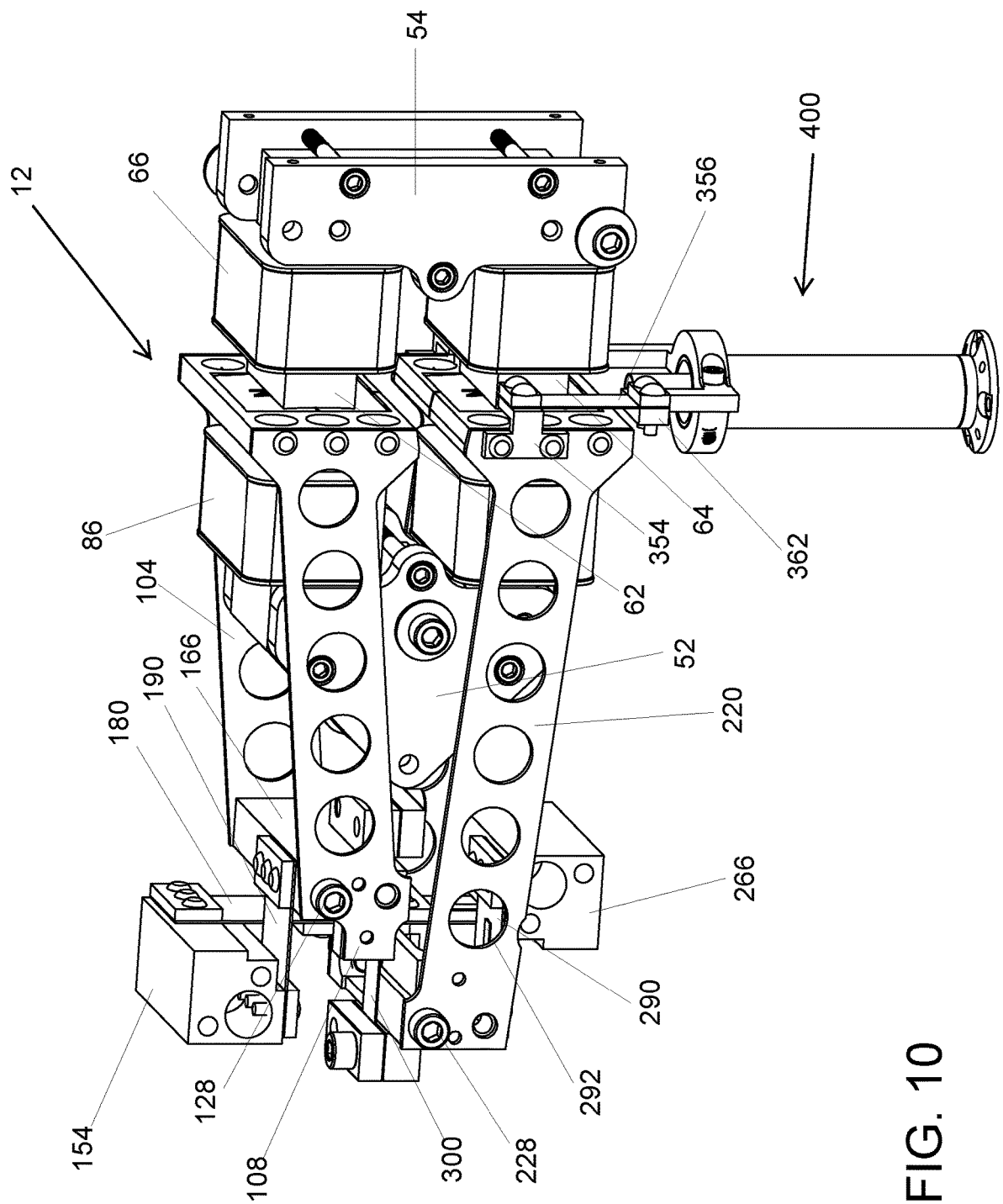
FIG. 10 is a perspective view of a linear magnet motor of the material testing apparatus in accordance with the present invention.
Figure 11:
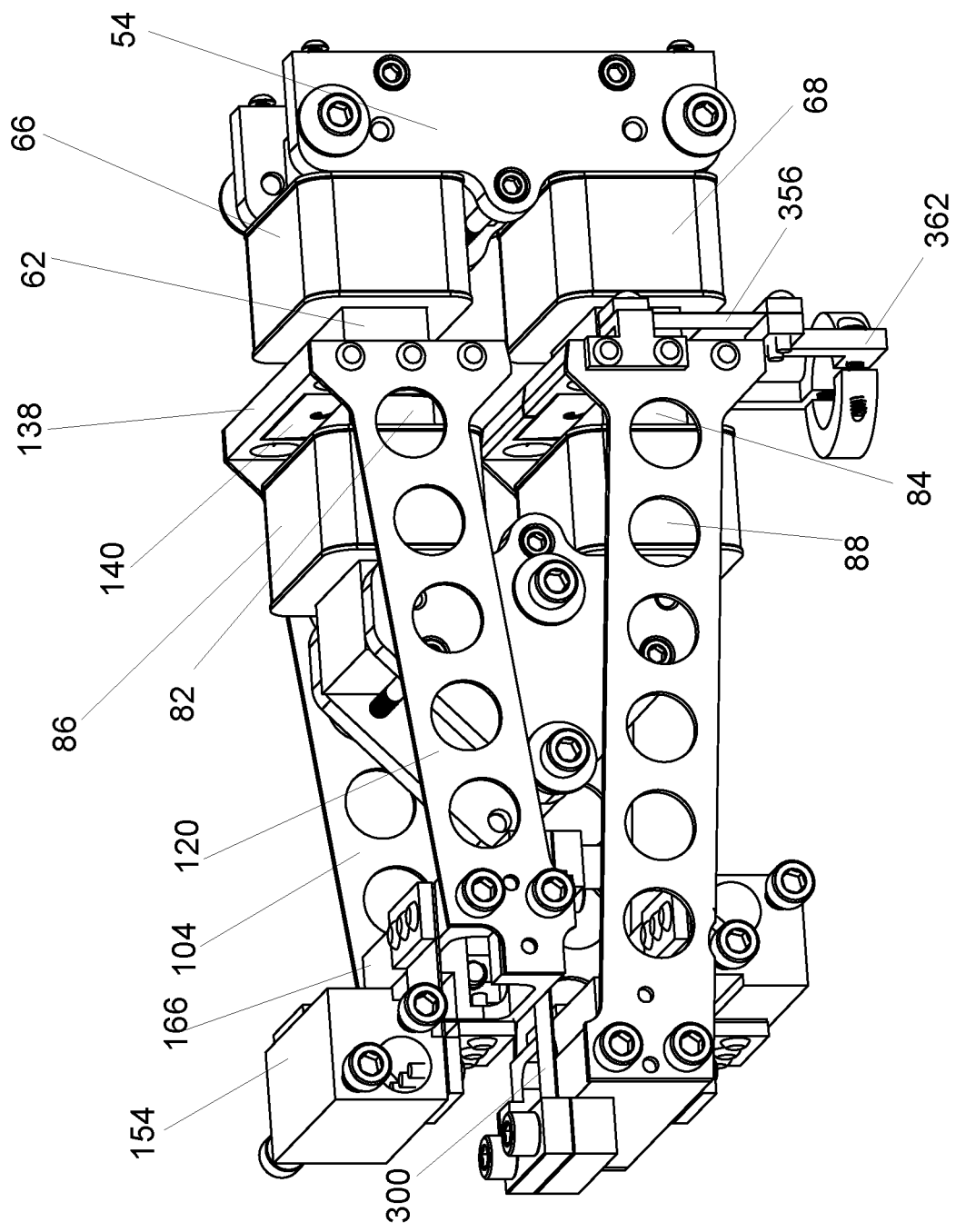
FIG. 11 is a perspective view of the linear magnet motor of the type shown in FIG. 10 and having the linear displacement assembly removed.
Figure 12:
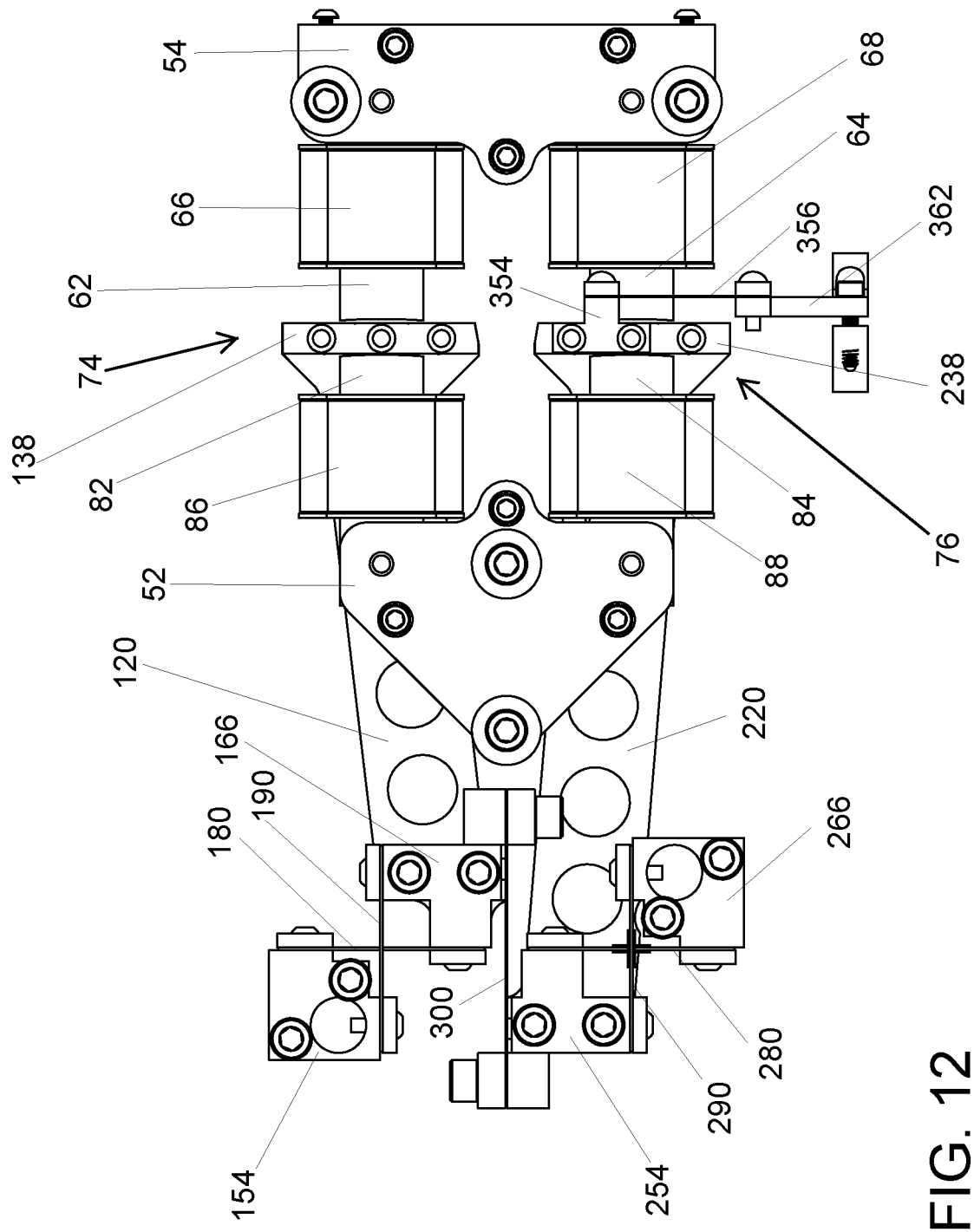
FIG. 12 is a side perspective view of the linear magnet motor of the type illustrated in FIG. 11 and having the left arms removed.
Figure 13:
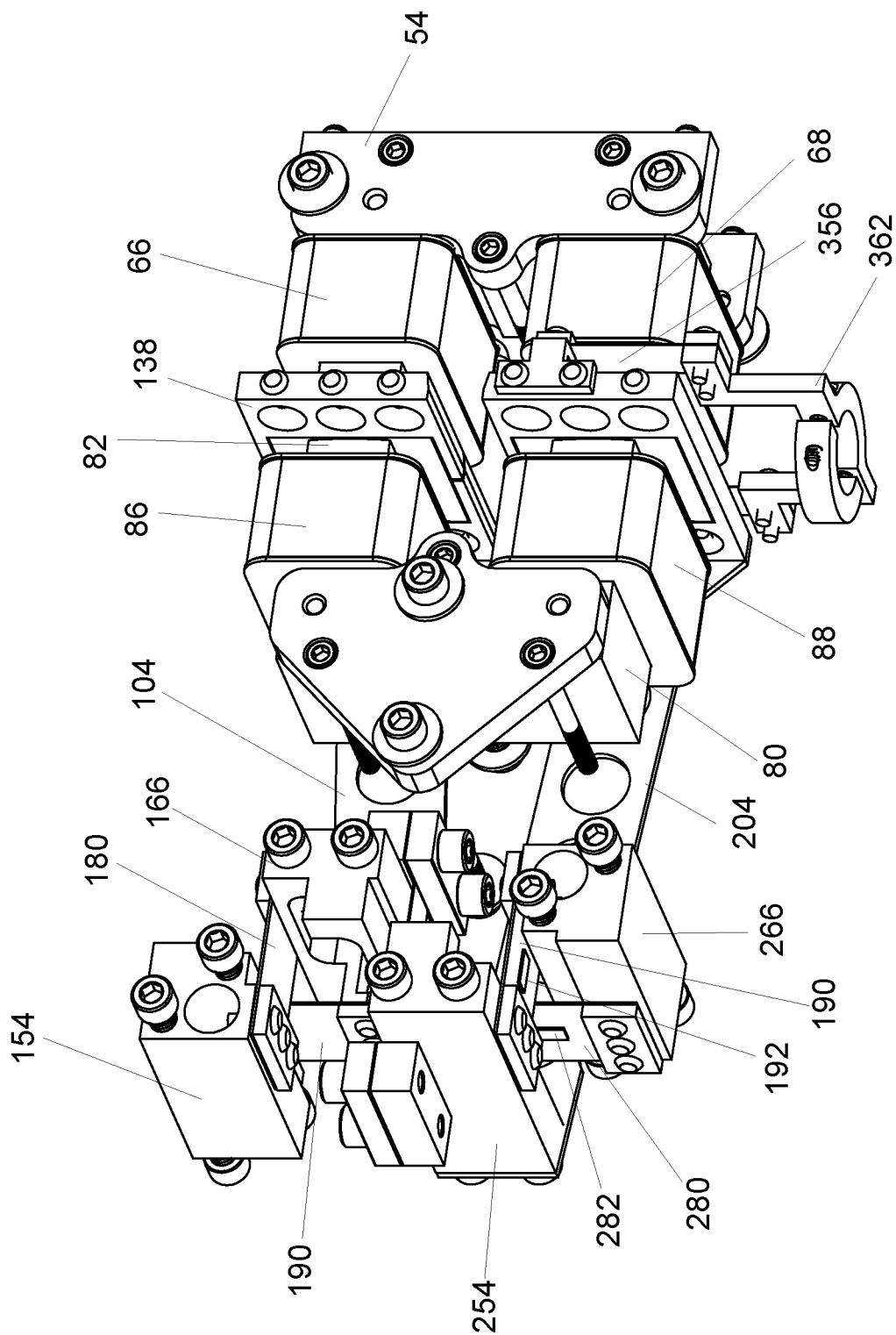
FIG. 13 is a back left perspective view of the linear magnet motor of the type illustrated in FIG. 11 and having the left arms removed.
Figure 14:
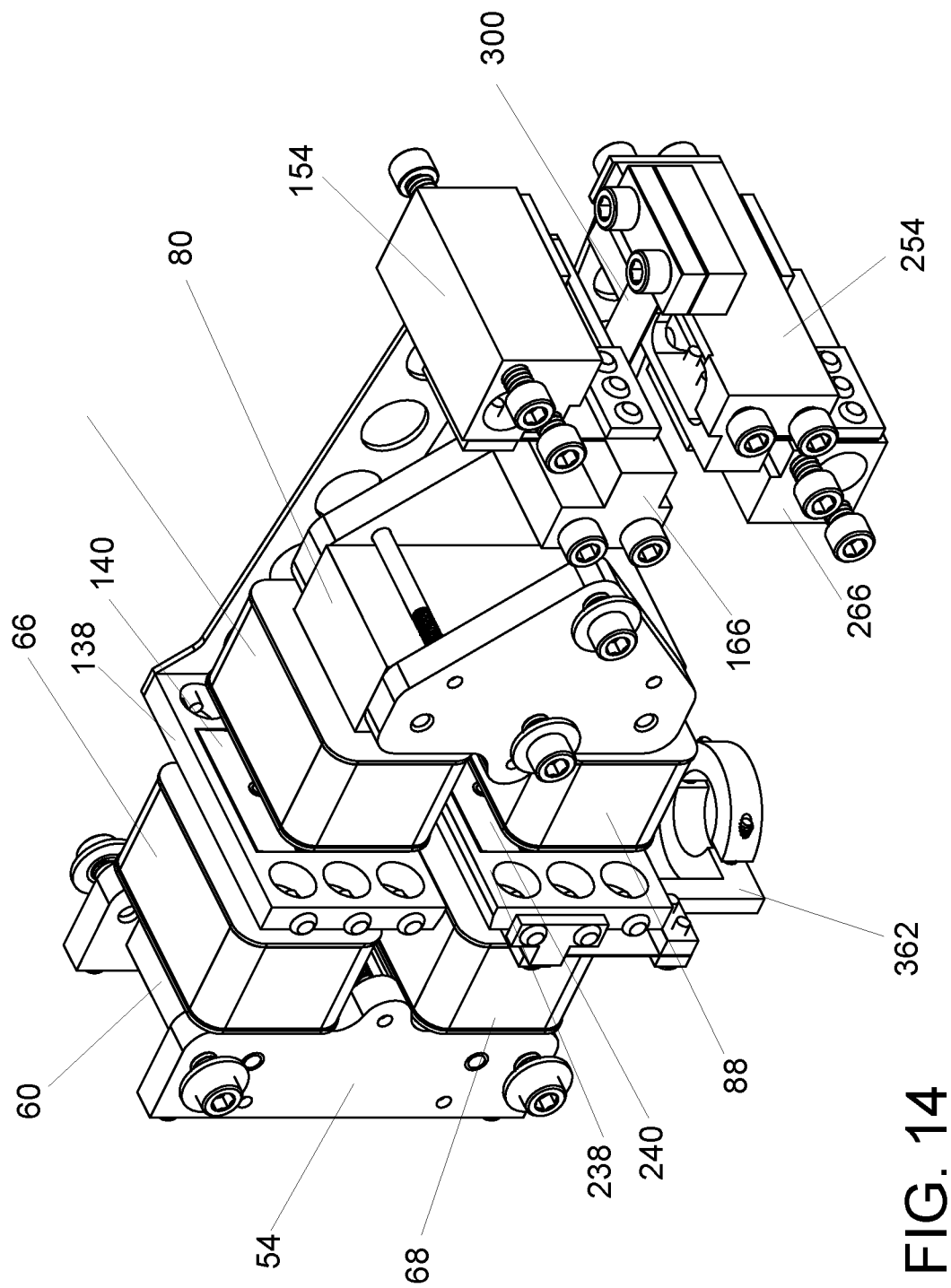
FIG. 14 is a back right perspective view of the linear magnet motor of the type illustrated in FIG. 11 and having the right arms removed.
Figure 15:
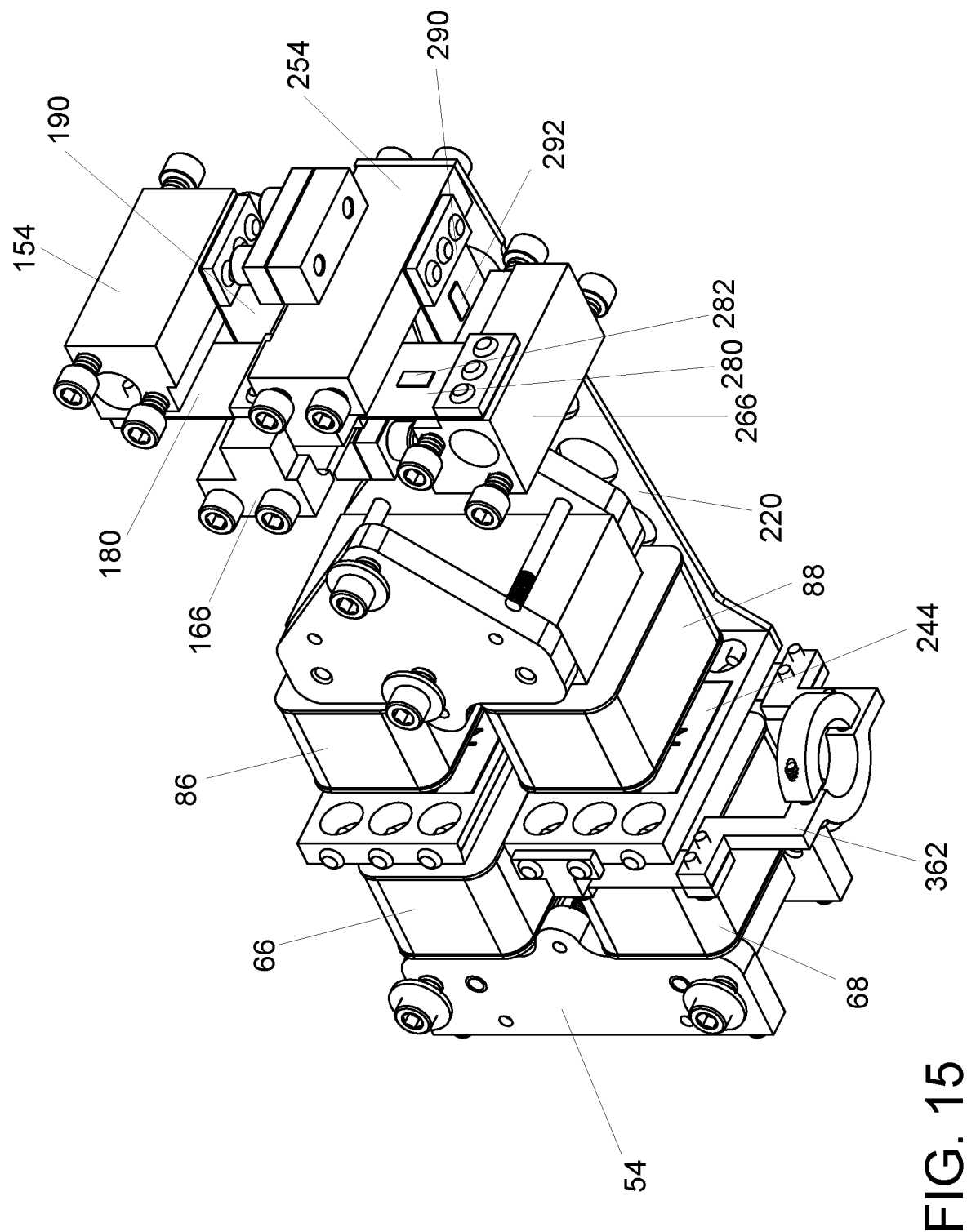
FIG. 15 is a bottom back right perspective view of the linear magnet motor of the type illustrated in FIG. 11 and having the right arms removed.
Figure 16:
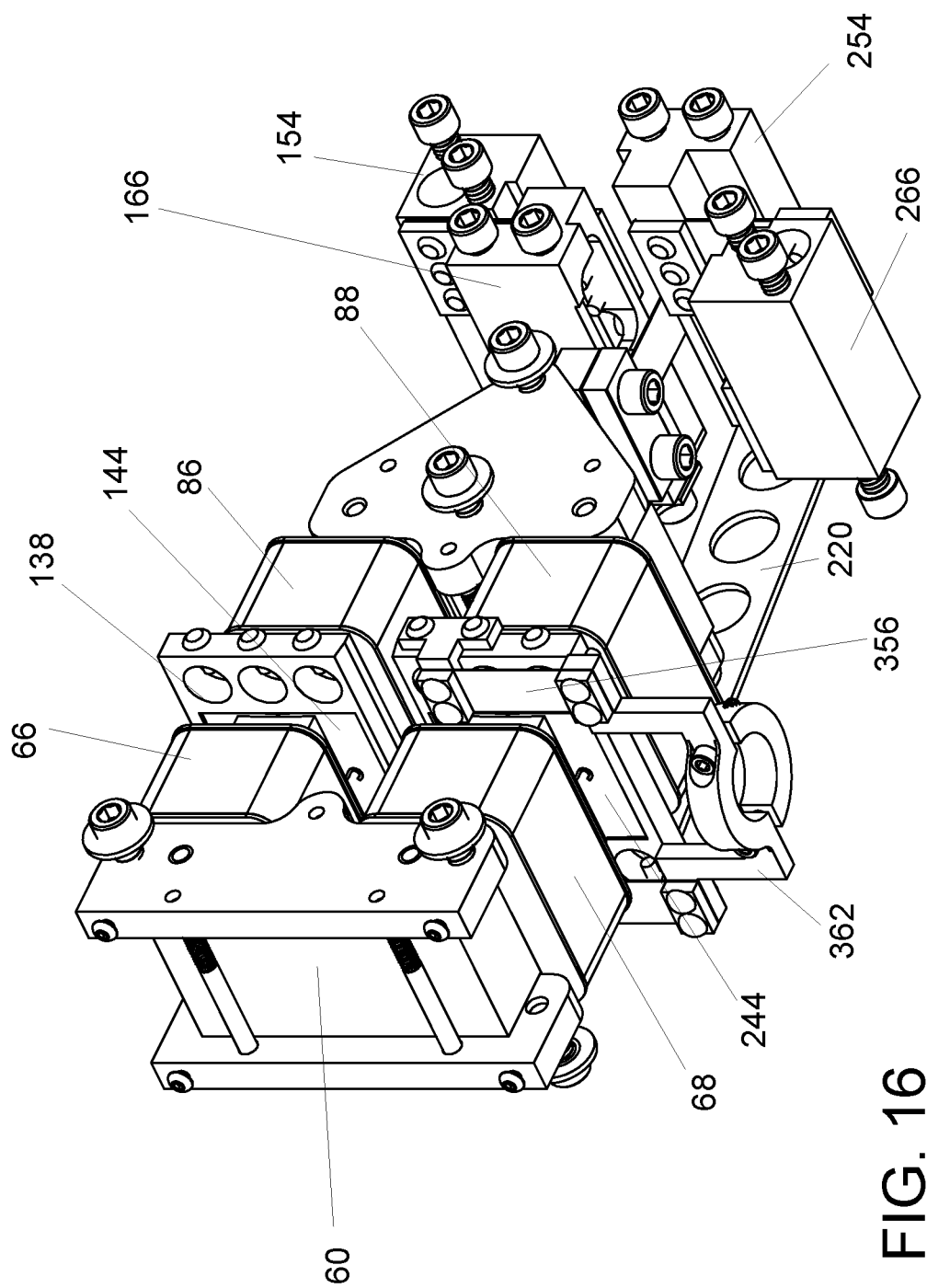
FIG. 16 is a bottom front right perspective view of the linear magnet motor of the type illustrated in FIG. 11 and having the right arms removed.
Figure 17:
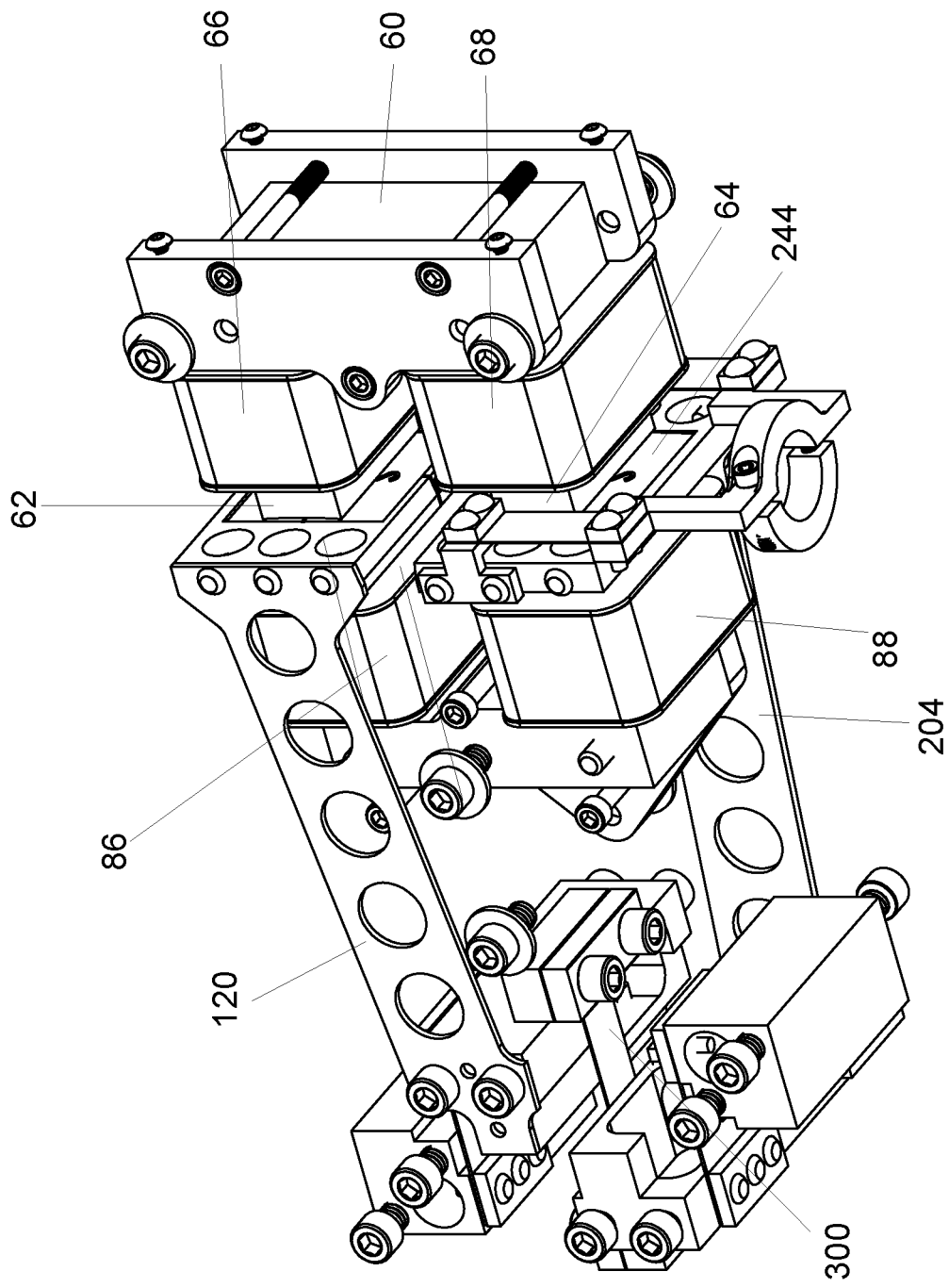
FIG. 17 is a bottom front left perspective view of the linear magnet motor of the type illustrated in FIG. 11 and having a bottom left arm removed.

Multiple components are attached to the external plates to affectively create an internal framework without requiring a separate dedicated frame. A lower end of column 24 is fixed to the base 22. The linear displacement assembly 400 is fixed to an upper end of the column 24 with linear bushing plate 360. The linear bushing plate 360 is also fixed or fastened to front side plates 38 and rear side plates 30. The left and right rear side plates vary slightly depending upon desired mounting holes to accommodate mounting of other components to the side plates. An upper portion of the side plates 30 are fixed to top plate 40, stator 50, a portion of cross-flexure assemblies 150 and 250, and top corner block 28 (see FIG. 2). Side covers 36 are fixed to the side plates 30 and the front side plates 38 are also fixed to stator 50. A window is formed in a portion of the rear side plates 30 and front side plates 38 through which a portion of the upper armature 100 and lower armature 200 of the linear actuator 12 extends. FIG. 3 illustrates the material testing apparatus 10 having the side covers 36 and right rear side plate 30 removed (exposing the controller chassis 31 and front side plate 38). A lower end portion of the back shroud 32 is fixed to base 22 and an upper portion of the back shroud is fixed to the top corner block 28 (see FIG. 4).

The input/output components 550 are fixed to the back shroud 32. The components include a micro controller 500, a 24V power supply 510 a 5V power supply 530, interconnect PCB 536, power supply on/off switch 512, usb ports 514, auxiliary ports 516, VGA monitor port 518, fan 520, Uninterruptable power supply sense line 532, ethernet port 534. Fan 520 includes a filter 522 and cover plate 524. Left A/C conditioner 542 and right DC conditioner 540 are fixed to top plate 40. An emergency stop switch 560 is mounted to front shroud 42. An LED array 564, including a power indicator 566, program running indicator 568, function generator running indicator 570 and fault indicator 572 are fixed to the front shroud 42 to provide a visual indication of the operational status when host computer 710 is not communicating with the test apparatus microcontroller.

The micro controller 500 includes a microcomputer 502, hard drive 504 and multifunction board 506. The microcomputer provides real-time operation of the test system. It monitors signal inputs provided by the multifunction board, generates test waveforms, makes PID calculations using the signal inputs and internally generated waveforms and outputs the results to the multifunction board. The test waveforms can either be sinusoidal, ramp, square, discrete levels or combinations thereof. The microcomputer can also store data using the hard drive 504 and upload/download data to/from a host computer using the ethernet port 534. Those skilled in the art will appreciate that the host computer may be coupled to multiple material testing apparatus 10 via a network switch 720.

The multifunction board 506 of material testing apparatus 10 uses A/D (analog to digital) convertors to convert the displacement, load and other transducer signals into digital readings that the microcomputer can use. Likewise, the multifunction board uses D/A (digital to analog) convertors to convert the drive signals provided by the microcomputer into analog signals that can be used to drive the test system. The multifunction board also includes digital input and digital output ports that can be used to monitor the Estop switch and uninterruptible supply status and to turn the linear motor amplifier 580 on/off and to actuate the LEDS.

The multifunction board is connected to the system conditioners and amplifier using the interconnect PCB 536 and ribbon cables (not shown).

In varying embodiments, the micro controller 500 is capable of controlling several operations, including, but not limited to linear motor control. The micro controller monitors the linear motor displacement using the LVDT assembly 430 that is integrated into the linear displacement assembly 400 or the one or more strain gages 282 and 292 that are bonded to each of the flexures 280 and 290 of the lower cross flexure assembly 250. The strain gages are wired into a Wheatstone bridge so that any rotation or pivot of the cross flexure creates a low-level output voltage that is proportional to the rotation. Due to the small rotation of the cross flexure, the linear displacement is approximately proportional to cross flexure rotation. When the LVDT is used to measure the linear displacement an AC Conditioner is used to excite the LVDT and create an analog output voltage that is proportional to the linear displacement assembly motion. When the strain gages mounted to the cross flexure are used to measure the cross-flexure rotation (hence linear displacement), the AC Conditioner is replaced by a DC Conditioner. The DC Conditioner applies an excitation voltage to the Wheatstone bridge and amplifies the resulting signal. The micro controller 500 also monitors the applied load using the load cell 48 mounted within the load sensing assembly 600. The micro controller 500 uses either the displacement or load signal as the feedback in a digital PID loop. The output signal from the PID loop is converted by the multifunction board 506 to drive the motor amplifier 580, which in turn drives the linear actuator 12.

Figure 37:
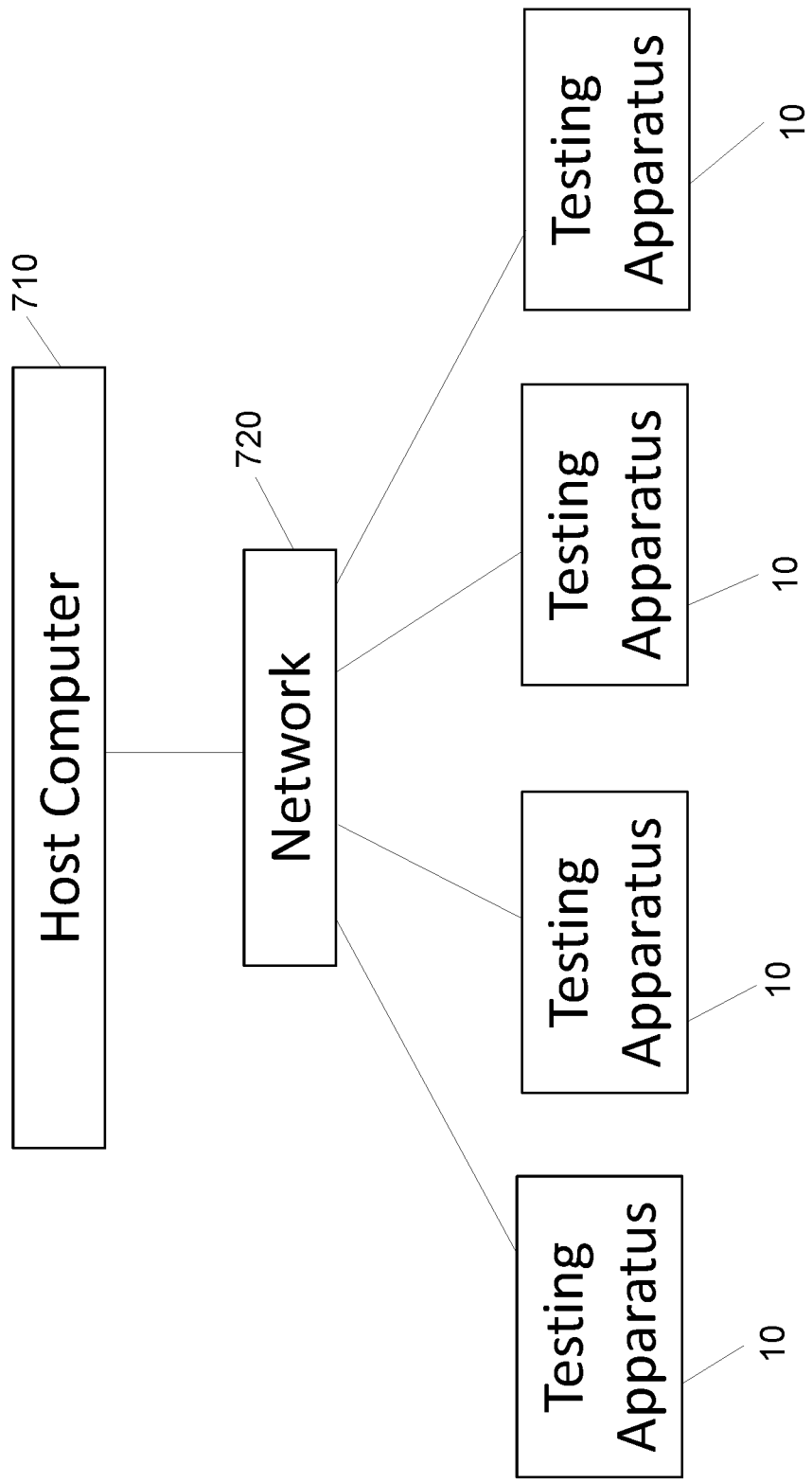
FIG. 37 is a block diagram illustrating a single host computer providing a user interface for controlling multiple test apparatus over a local area network (LAN).

The micro controller 500 communicates with the host computer 710 via the ethernet port 534. The host computer provides the user a graphical user interface (GUI) for running the material test apparatus via a software program which runs on the host computer. The host computer is capable of operating one or more test apparatuses. The GUI enables the user to select the desired material test apparatus to be operated, turn the test apparatus on/off, set limits, setup and run test waveforms, and to gather, display and store data generated by the test apparatus. The host computer is typically a laptop computer and typically includes a keyboard, a mouse or other select device, a monitor and hard drive. The host computer and test apparatus micro controller(s) communicate using TCPIP and UDP protocols. When only one material testing apparatus is connected to the host computer, the ethernet port 534 of the microcontroller is connected directly to the ethernet port of the host computer using a crossover cable. When two or more test apparatuses are connected to the host computer a network switch 720 is connected to the host computer ethernet port and ethernet ports 534 of the test apparatus (see, for example, FIG. 37). It should also be noted that the host computer can be connected to the laboratory computer network or an external network using a second separate ethernet adapter.

Referring next to FIGS. 9-25 the linear actuator 12 will be described in greater detail. Linear actuator 12 includes an upper armature 100, lower armature 200 and stator 50. Upper armature 100 includes spaced apart right and left arms 104 and 120. A distal end 106 of right arm 104 is fixed to cross-flexure block 166 of cross flexure assembly 150 and a free end 108 is fixed to magnet bracket or frame 138. Similarly, a distal or fixed end of left arm 120 is fixed to cross flexure block 166 of cross flexure assembly 150 and a free end is fixed to magnet bracket or frame 138. The ends extend upward at a slight angle from the center axis to allow the upper armature to be oriented above a center horizontal axis of the linear actuator 12. The magnet bracket or frame 138 contains a set of permanent magnets 140. The set of permanent magnets includes a top permanent magnet 142 and bottom permanent magnet 144. The top permanent magnet 142 has its north magnetic pole facing towards the front of the material test apparatus while the south magnetic pole faces distal towards its cross-flexure assembly 150. The bottom permanent magnet 144 has its north magnetic pole facing towards the cross-flexure assembly 150 while the south magnetic pole faces forward towards the front of the material test apparatus.

Lower armature 200 includes spaced apart right and left arms 204 and 220. A distal end of right arm 204 is fixed to cross flexure block 266 of cross flexure assembly 250 and a free end is fixed to magnet bracket or frame 238. Similarly, a distal end of left arm 220 is fixed to cross flexure block 266 of cross flexure assembly 250 and a free end is fixed to magnet bracket or frame 238. The ends extend downward at slight angle from the center horizontal axis to allow the lower armature to be oriented below a center axis of the linear actuator 12. The magnet bracket or frame 238 contains a set of permanent magnets 240. The set of permanent magnets includes a top permanent magnet 242 and bottom permanent magnet 244. The top permanent magnet 242 has its north magnetic pole facing towards the front of the material test apparatus while the south magnetic pole faces distal towards its cross-flexure assembly 250. The bottom permanent magnet 244 has its north magnetic pole facing towards the cross-flexure assembly 250 while the south magnetic pole faces forward towards the front of the material test apparatus.

Figure 18:
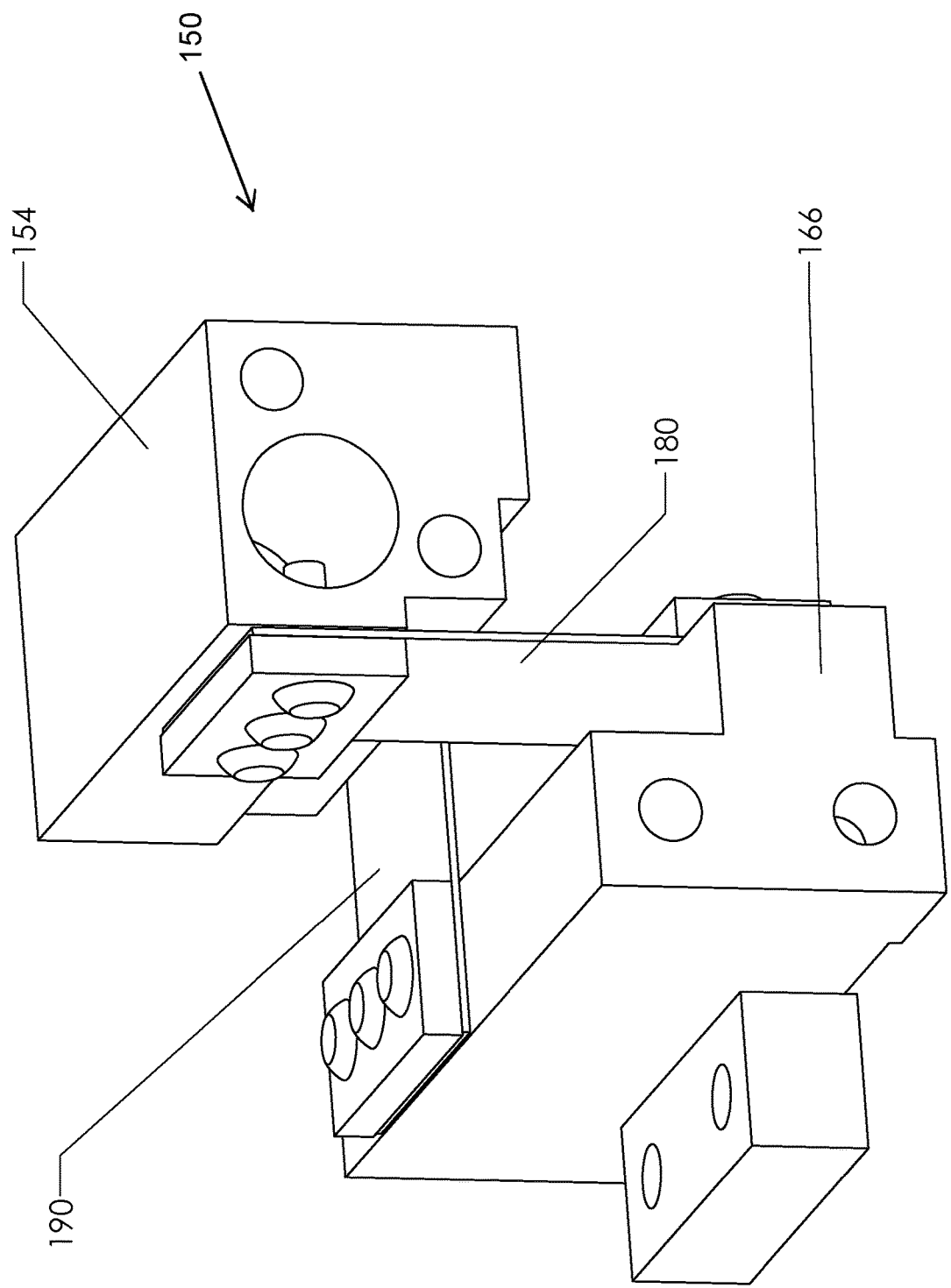
FIG. 18 is a top perspective view of a top cross-flexure assembly of the linear magnet motor of the material testing apparatus in accordance with the present invention.
Figure 19:
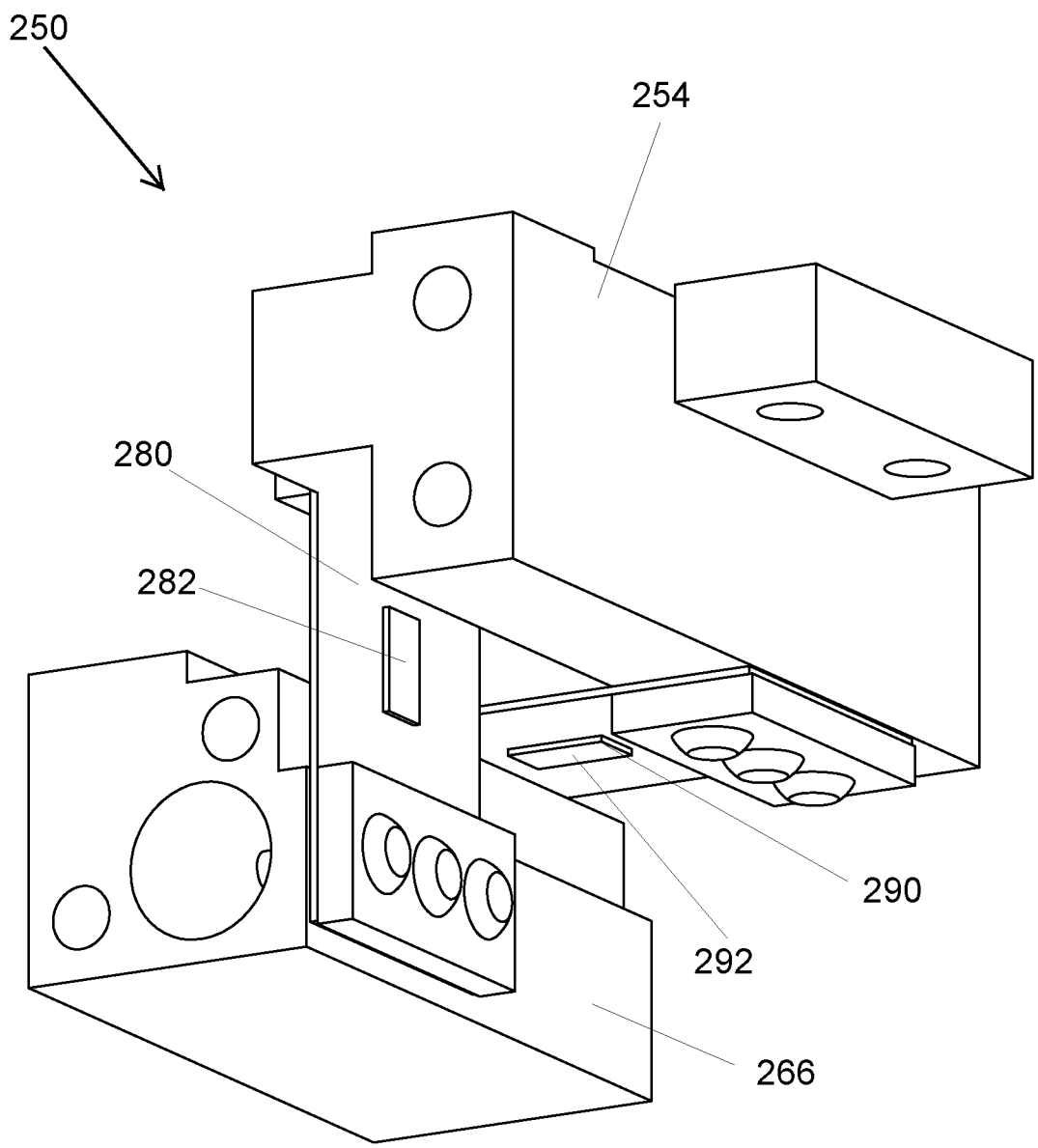
FIG. 19 is a bottom perspective view of a bottom cross-flexure assembly of the linear magnet motor of the material testing apparatus in accordance with the present invention.
Figure 20:
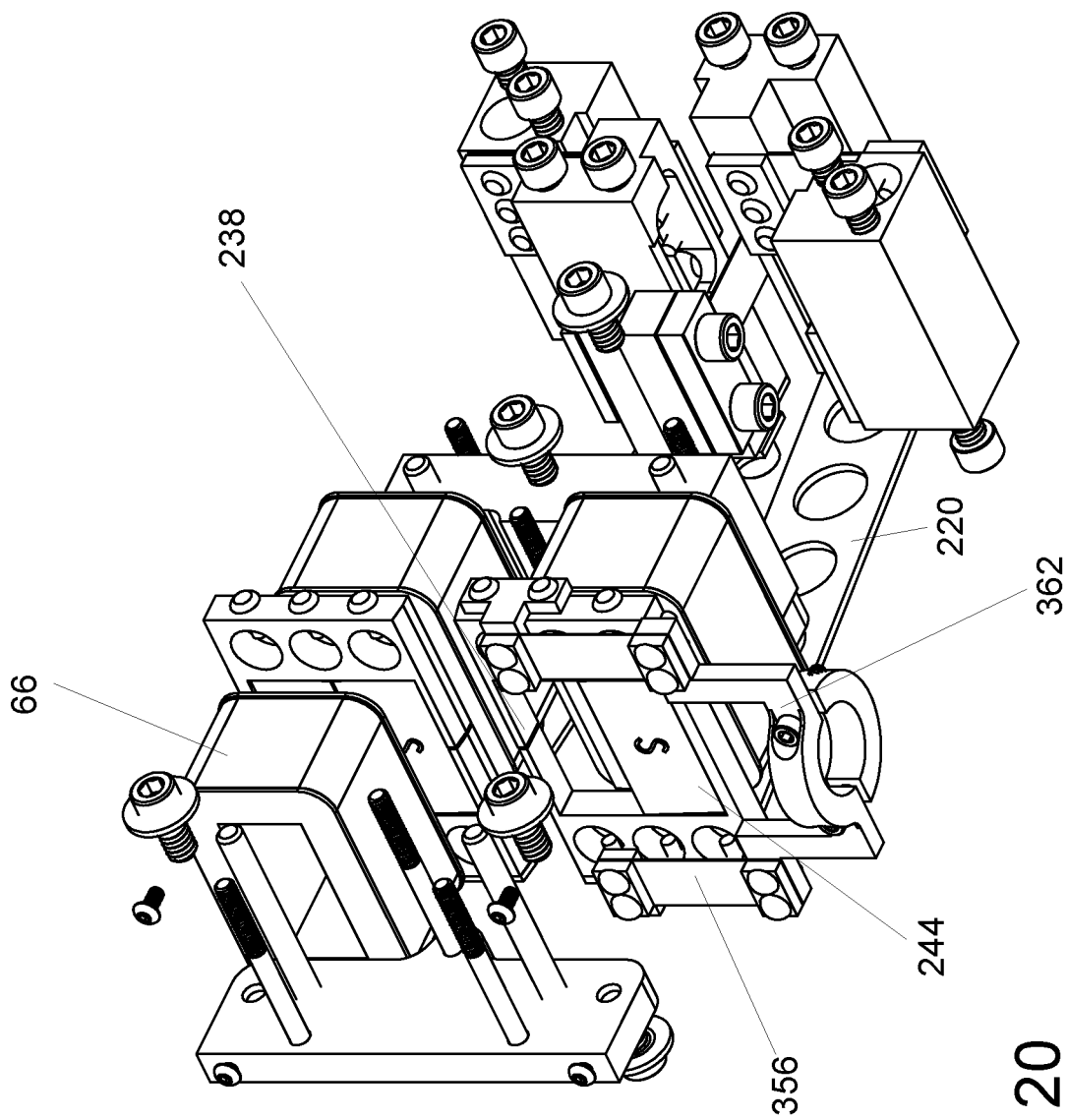
FIG. 20 is a bottom front right perspective view of the linear magnet motor of the material testing apparatus in accordance with the present invention and illustrating the right arms, the front c-shaped stator core, the bottom front end coil of the c-shaped core, and one of the permanent magnets removed.
Figure 21:
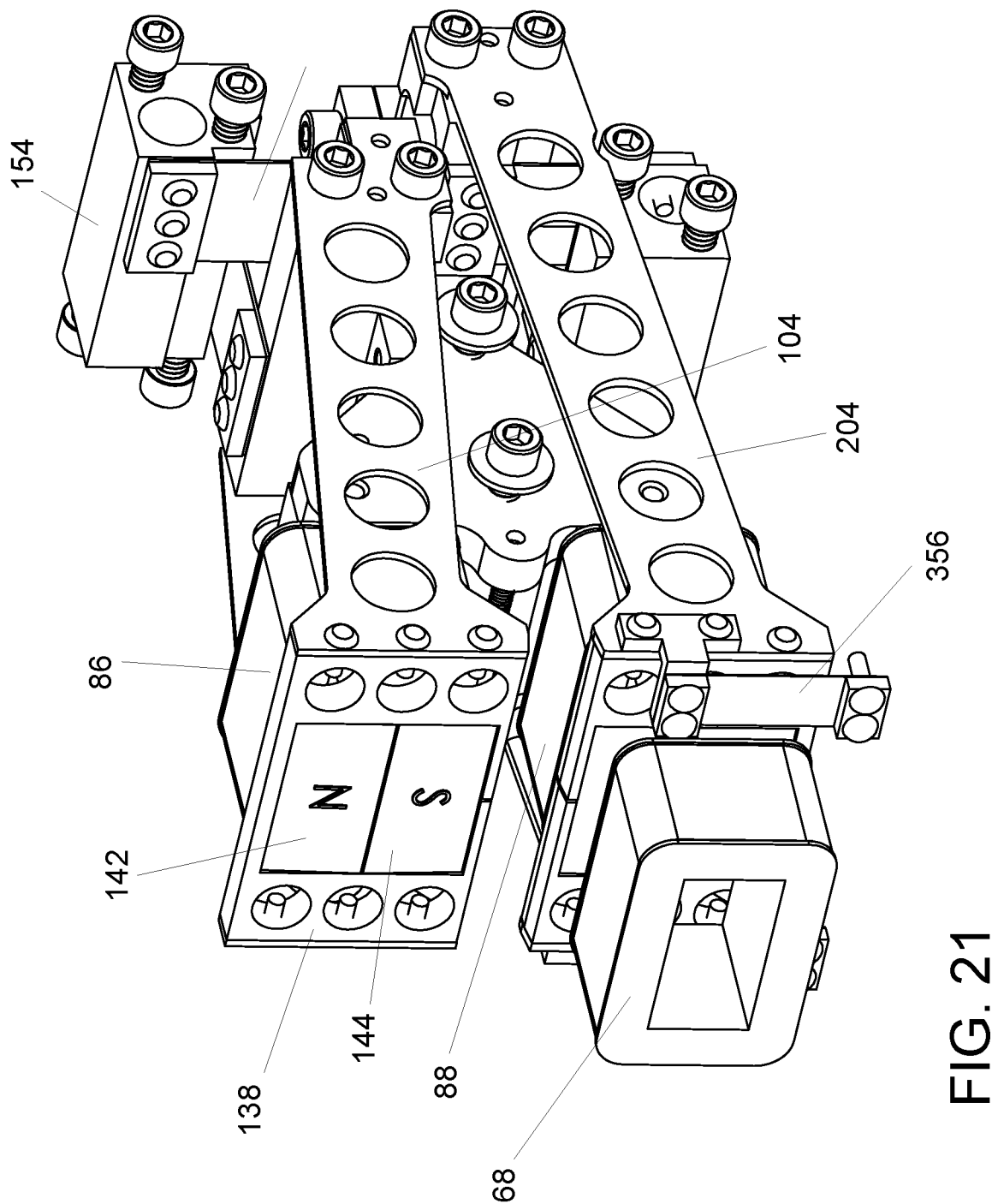
FIG. 21 is a front right perspective view of a portion of the linear magnet motor of the material testing apparatus in accordance with the present invention and illustrating the front stator core and top coil removed.
Figure 22:
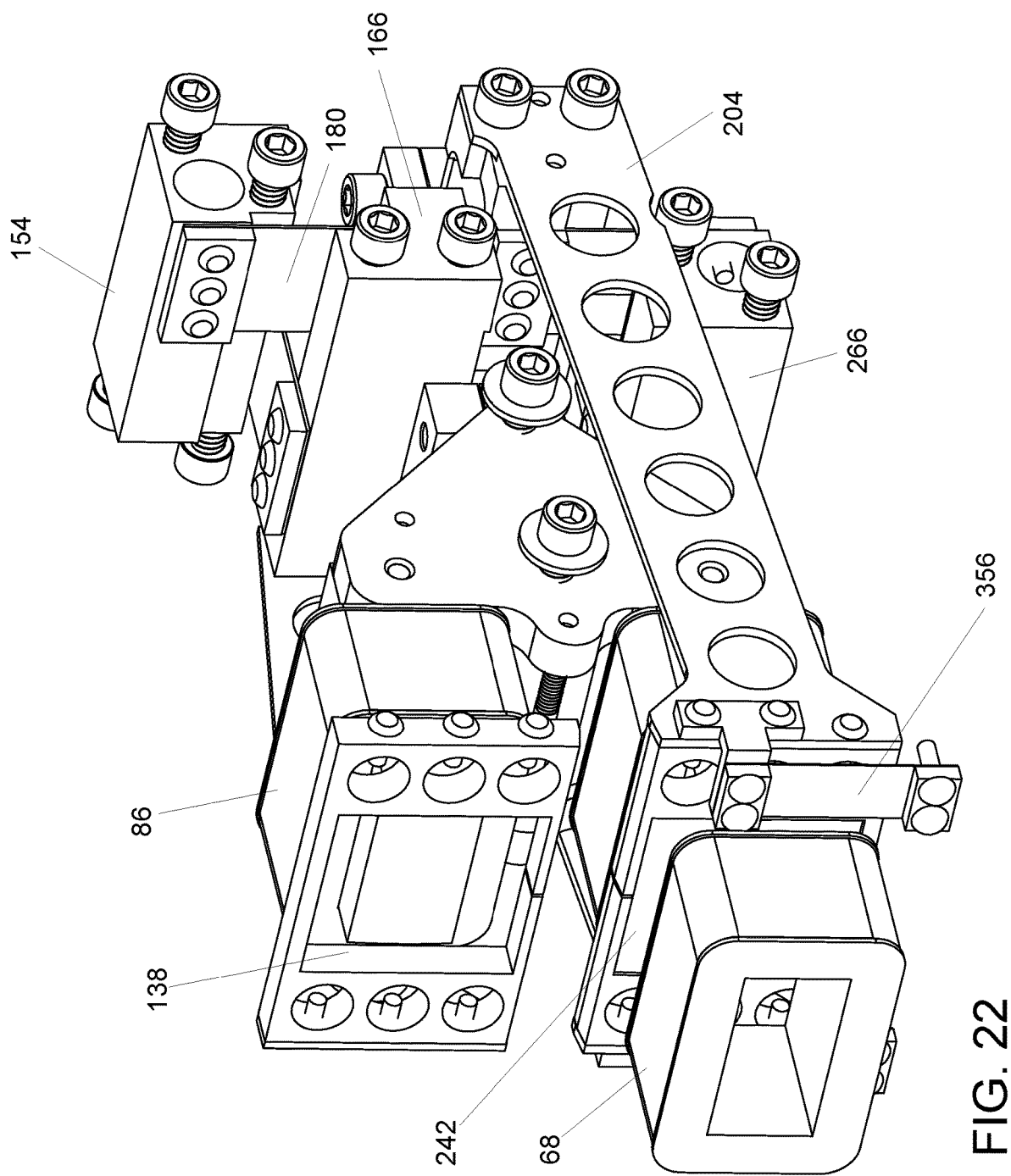
FIG. 22 is a front right perspective view of a portion of the linear magnet motor of the material testing apparatus in accordance with the present invention and illustrating the front stator core, top right arm, permanent magnet set, and top front coil removed.
Figure 23:
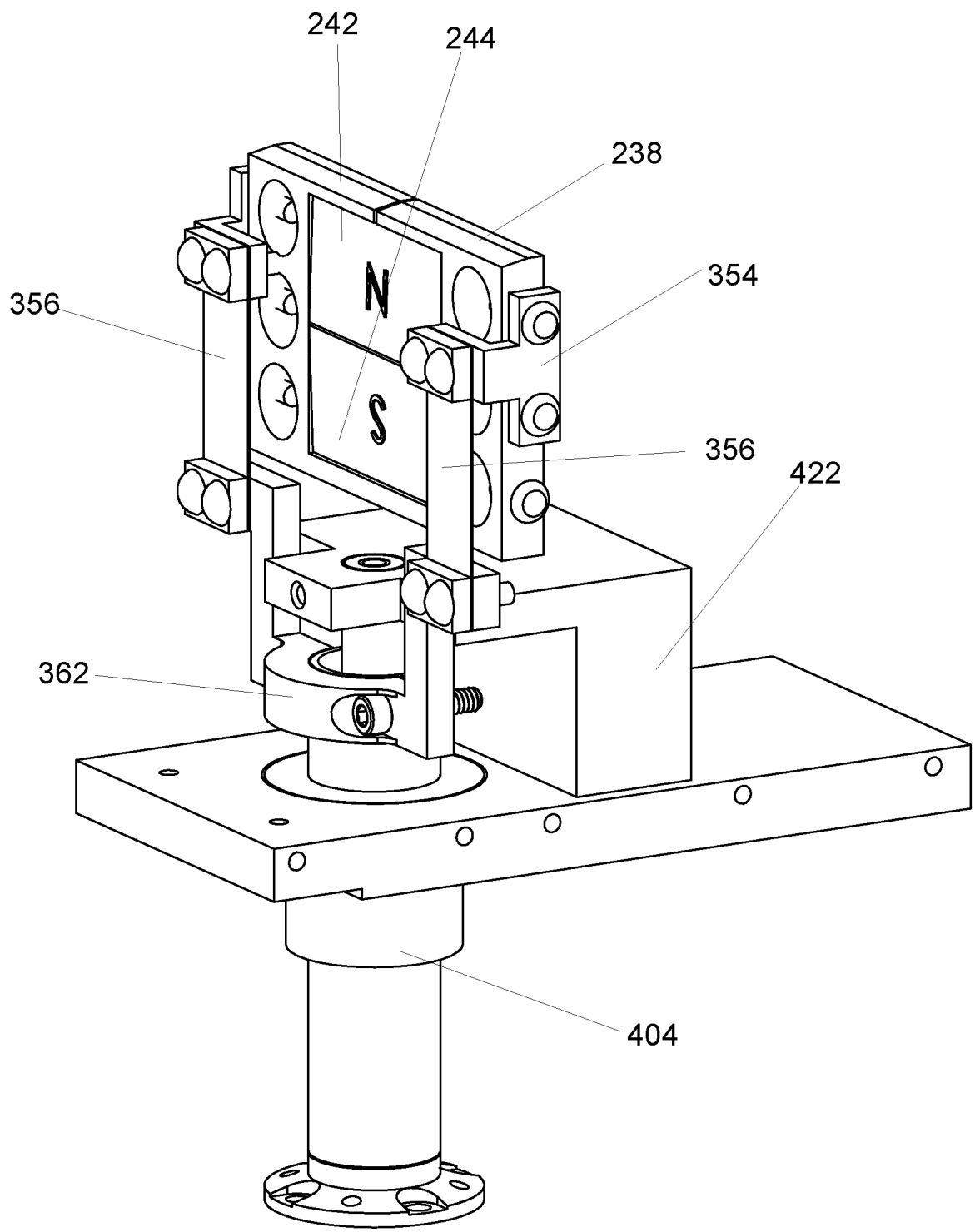
FIG. 23 is a right perspective view a portion of the linear displacement assembly of the material testing apparatus in accordance with the present invention and shown coupled to a front mounting bracket of the lower armature of the linear magnet motor.
Figure 24:
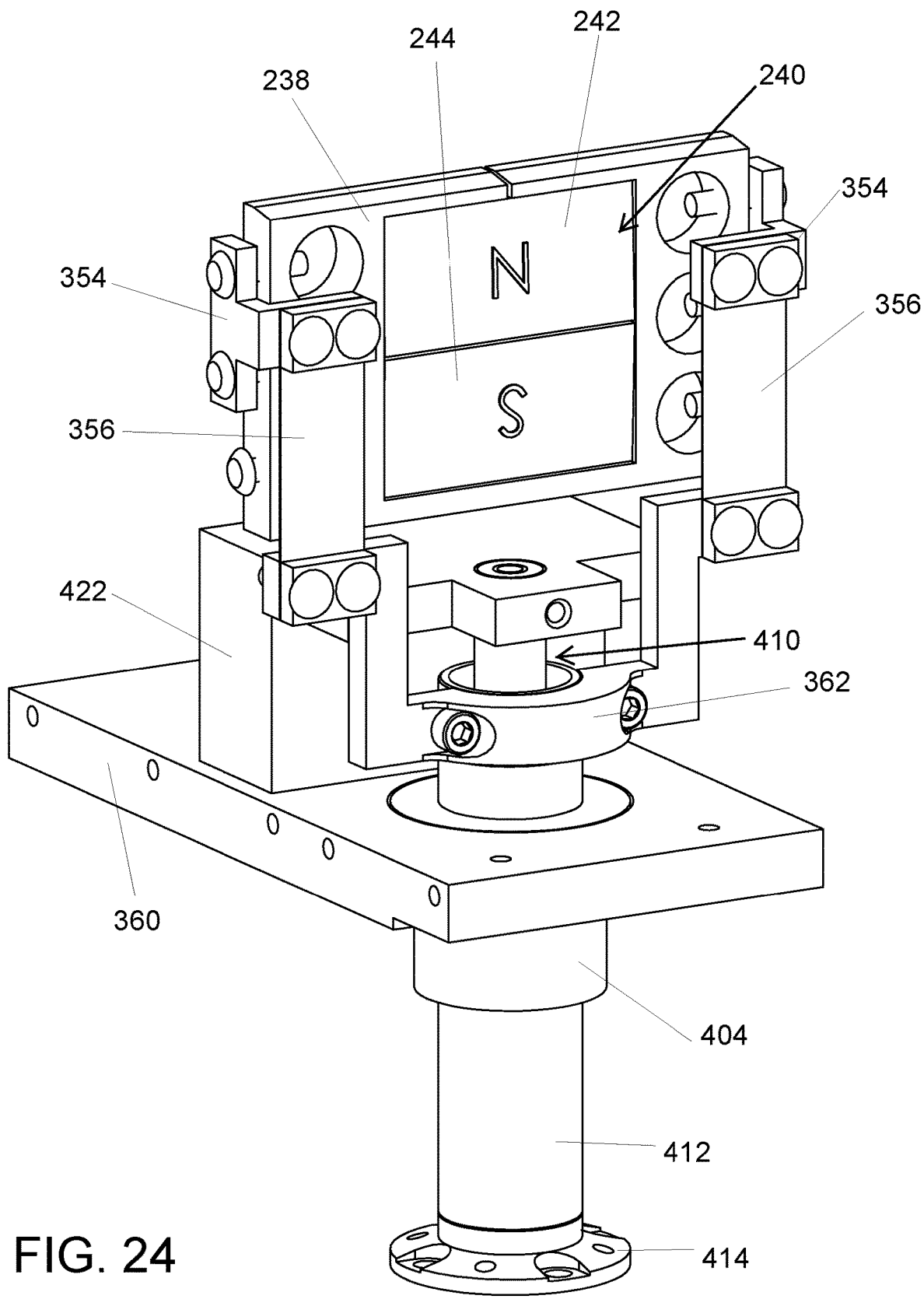
FIG. 24 is a front perspective view of the linear displacement assembly of the type shown in FIG. 23.
Figure 25:
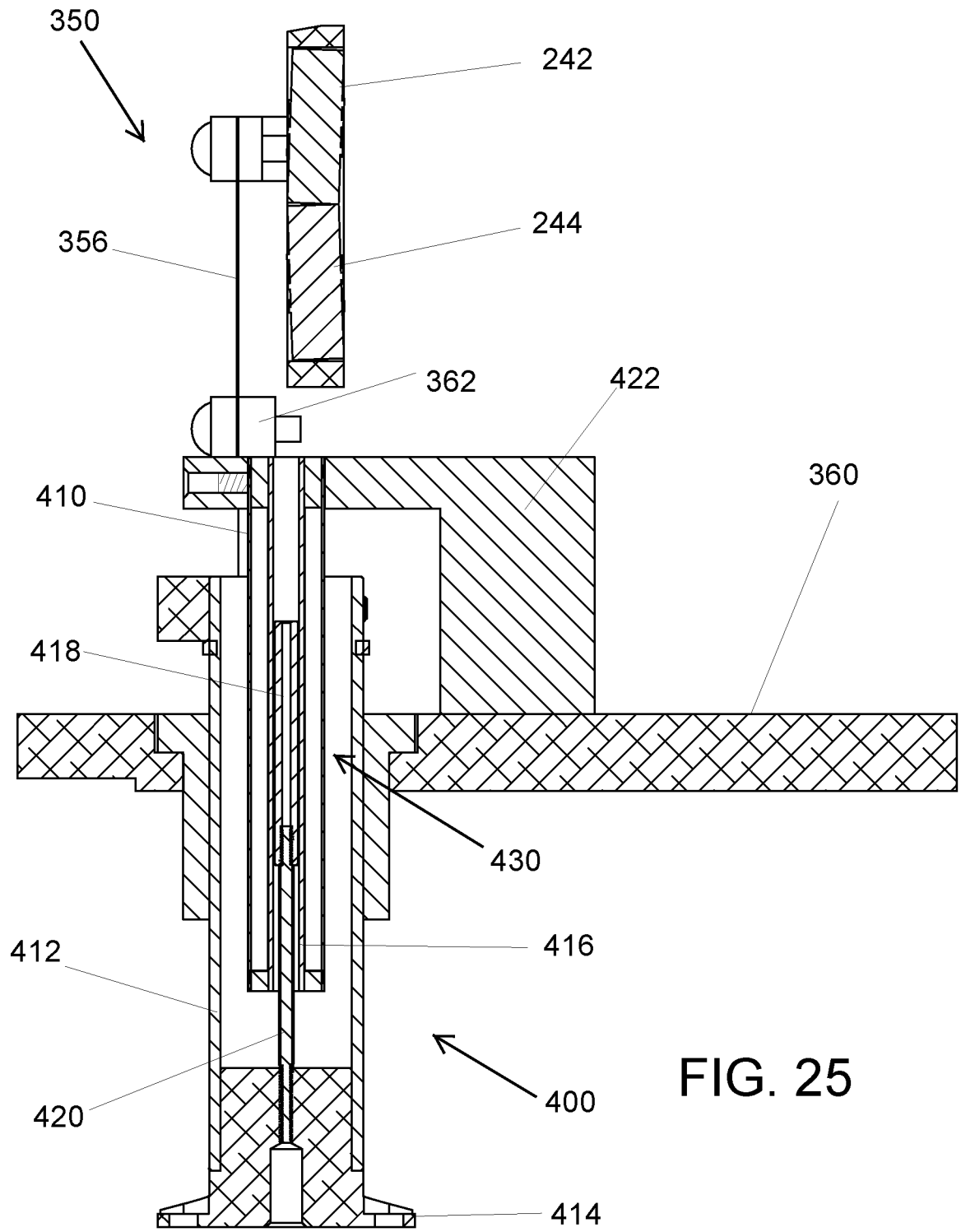
FIG. 25 is a partial sectional side elevational view of the linear displacement assembly of the type shown in FIG. 23.

Cross-flexure assembly 150 of upper armature 100 includes a top block 154 and bottom block 166 (see FIG. 18). The top block 154 is mounted to the left and right side plates 30. The top block 154 and bottom block 166 are interconnected with a vertical flexure 180 and horizontal flexure 190. Cross-flexure assembly 250 of lower armature 200 includes a top block 254 and bottom block 266 (see FIG. 19). The bottom block 266 is mounted to the left and right side plates 30. The top block 254 and bottom block 266 are interconnected with a vertical flexure mount 280 and horizontal flexure 290. Vertical flexure includes one or more strain gauges 282 and horizontal flexure includes one or more strain gauges 292 fixed thereto.

Referring to FIGS. 2-24 and in particular FIGS. 20-24, stator 50 includes a forward c-shaped core 60 and rearward c-shaped core 80. The forward c-shaped core 60 includes a forward frame mount 54 that attaches to front side plates 38. The rearward c-shaped core 80 includes a rearward frame mount 52 that attaches to left and right side plates 30. Forward c-shaped core 60 includes a top end of core 62 and bottom end of core 64. A set of top wire windings or coil 66 is positioned near the end of the top end of the core 62 and a set of bottom wire windings or coil 68 is positioned near the end of the bottom end of the core 64. Similarly, the rearward c-shaped core 80 includes a top end of core 82 and bottom end of core 84. A set of top wire windings or coil 86 is positioned near the end of the top end of the core 82 and a set of bottom wire windings or coil 88 is positioned near the end of the bottom end of the core 84. The forward c-shaped core 60 and rearward c-shaped core 80 are spaced apart with the top ends 62 and 82 and bottom ends 64 and 84 aligned but spaced apart to form top gap 74 and bottom gap 76. Magnet frame 138 and permanent magnet set 140 are spaced apart but aligned in the top gap 74 and magnet frame 238 and permanent magnet set 240 are spaced apart but aligned in the bottom gap 76.

The four coils 66, 68, 86, and 88 are electrically connected in series although they could be electrically connected in parallel. When a current flows through the coils about the cores 60 and 80, magnetic fields form in the gaps 74 and 78. The direction of the current may be altered so that the magnetic field acts against the permanent magnet's fields 140 and 240 in a way that the first armature 100 moves up and down while the lower armature conversely moves down and up. When the upper armature 100 moves up or down the vertical and horizontal flexures 180 and 190 bend. Likewise, when the lower armature moves down or up the vertical flexure and horizontal flexure 280 and 290 bend.

Flexure 300 interconnects cross flexure assembly 150 to cross flexure assembly 250. In this manner when the cross-flexure assembly 150 bends a displacement and/or force translates to the lower armature 200. However, because the upper armature 100 and lower armature have approximately the same mass and move in opposing directions, the accelerations of the two magnet assemblies effectively cancel each other thereby eliminating potential vibration from movement of the armatures 100 and 200. As the flexures 280 and 290 bend the strain gages 282 and 292 measure the strain on the flexure. Without limitation intended the strain gages mounted on lower cross-flexure assembly 250 are wired in a Wheatstone bridge configuration (much like a load cell or extensometer) to provide an output voltage that is proportional to the amount of bending. The output voltage is used by micro controller 500 to control an amount of desired movement of the linear displacement assembly 400.

With reference to FIGS. 24-27, load transfer flexure assembly 350 interconnects the lower armature 200 to the linear displacement assembly 400.

An arm mount 354 connects transfer flexure 356 to the lower armature 200 and a flexure interconnect 362 couples the other end of transfer flexure 356 to push/pull tube 412. When a current is applied to the stator 50, the combined force from movement of the upper and lower armatures 100 and 200 translates to linear motion of portions of the displacement assembly 400. The linear displacement assembly includes a linear sleeve bushing 404, push/pull tube 412, and upper grip attachment point 414 and Linear Variable Differential Transformer (LVDT) assembly 430. The LVDT assembly includes an external casing 410, the winding body 416, core 418 and core extension rod 420 which connects to the upper grip attachment point 414. The external casing 410 and winding body 416 are coupled to LVDT fixation mount 422 which is attached to the linear bushing plate 360. The LVDT provides a method for measuring the position of the push/pull tube of the load assembly. The lower strain-gaged cross-flexure assembly provides an alternate method of measuring the push/pull tube position. In this manner the amount of linear displacement of the specimen may be monitored and controlled.

Figure 26:
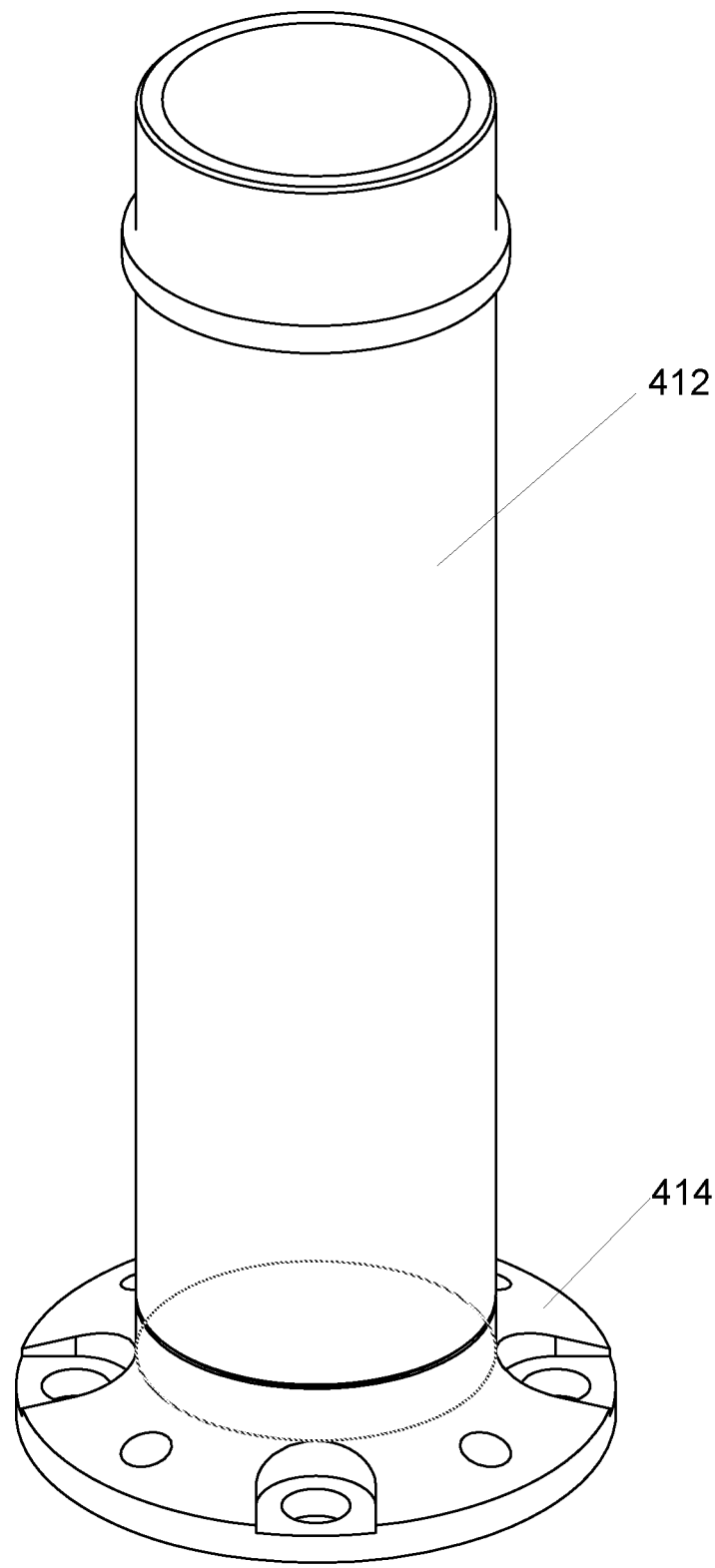
FIG. 26 is a perspective view of the push/pull tube of the linear displacement assembly of the material testing apparatus in accordance with the present invention.
Figure 27:
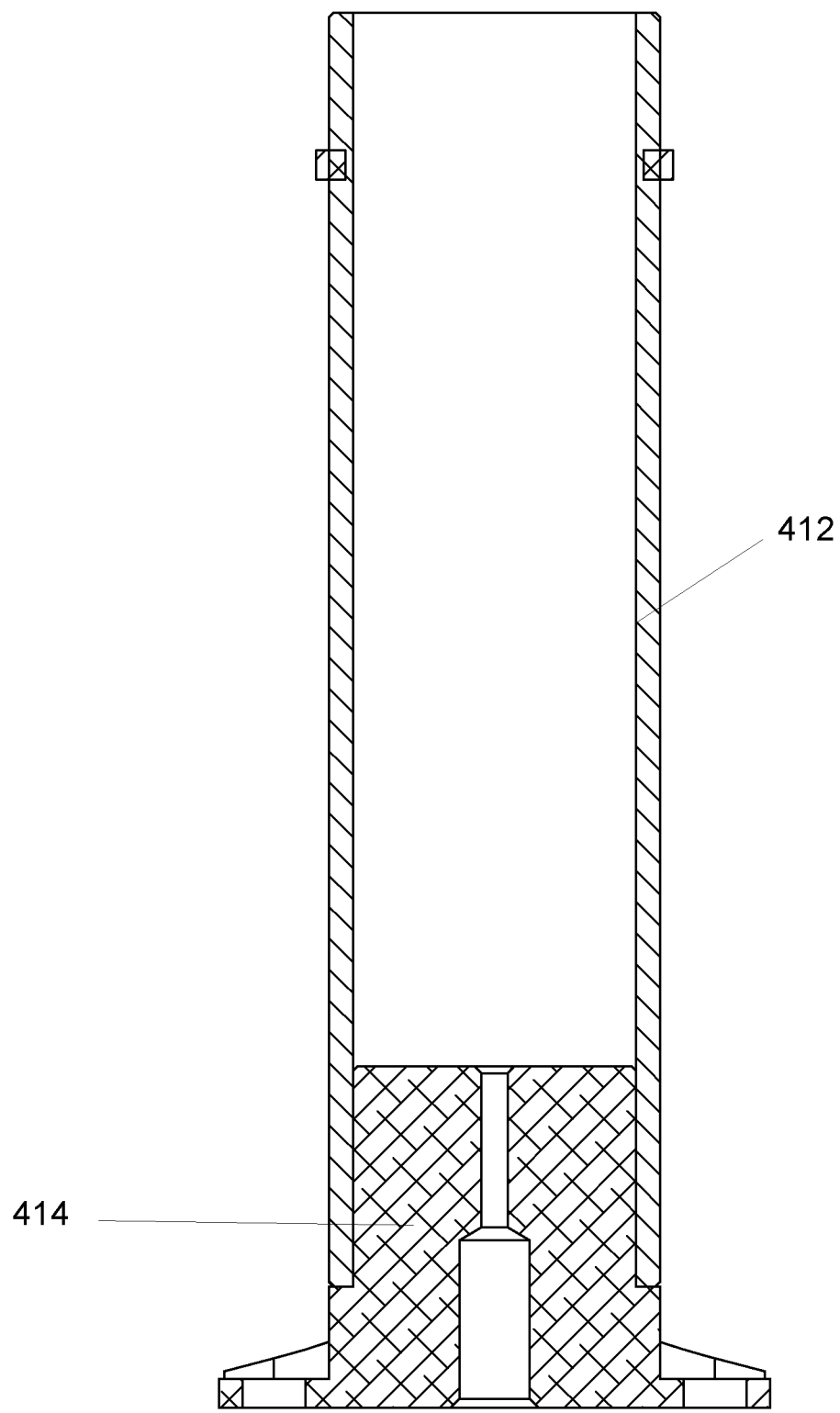
FIG. 27 is a partial sectional side elevational view of the push/pull tube of the type shown in FIG. 26.
Figure 28:
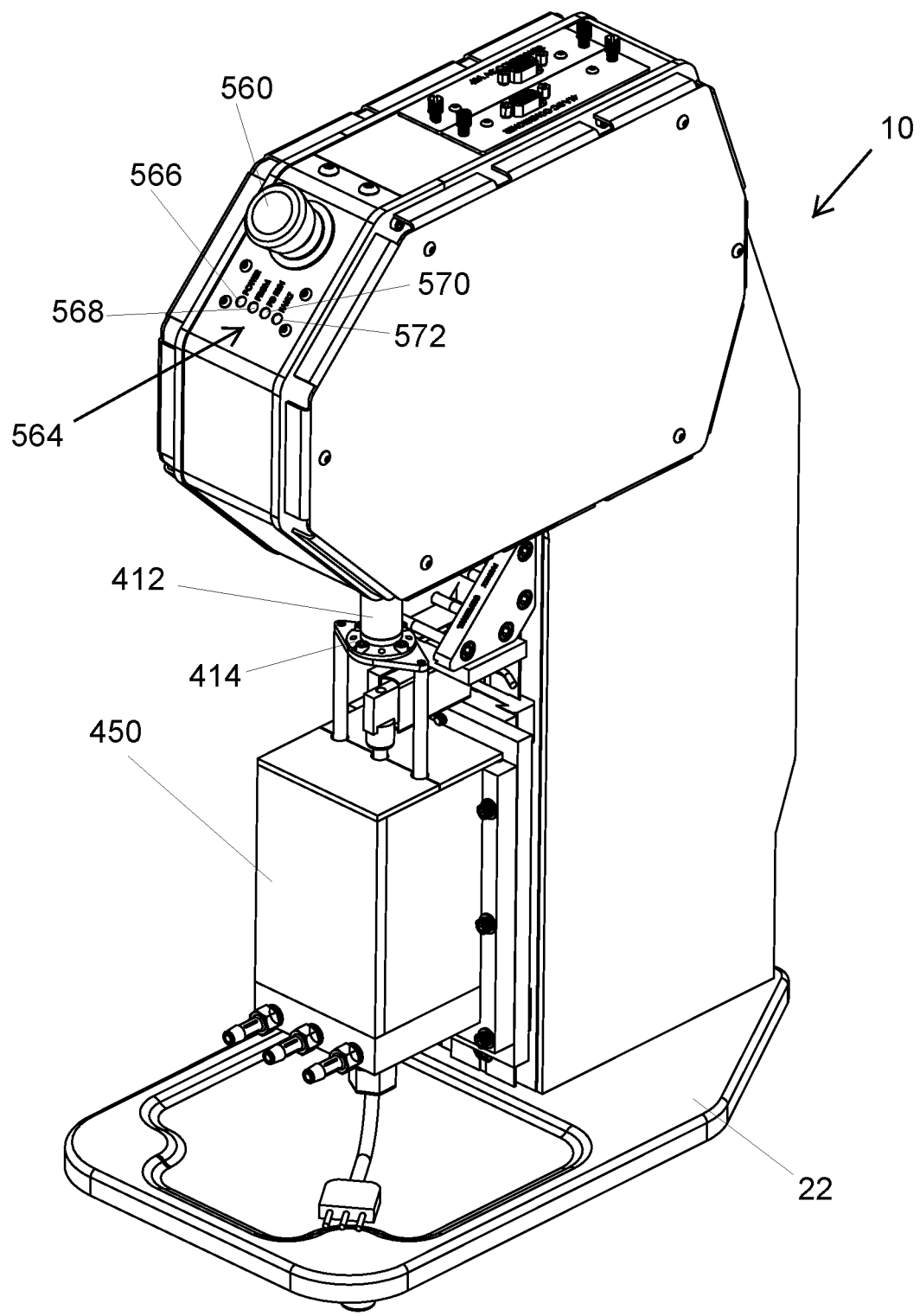
FIG. 28 is a front right top perspective view of a material testing apparatus in accordance with the present invention and having an environmental chamber mounted to the column of the material testing apparatus.
Figure 29:
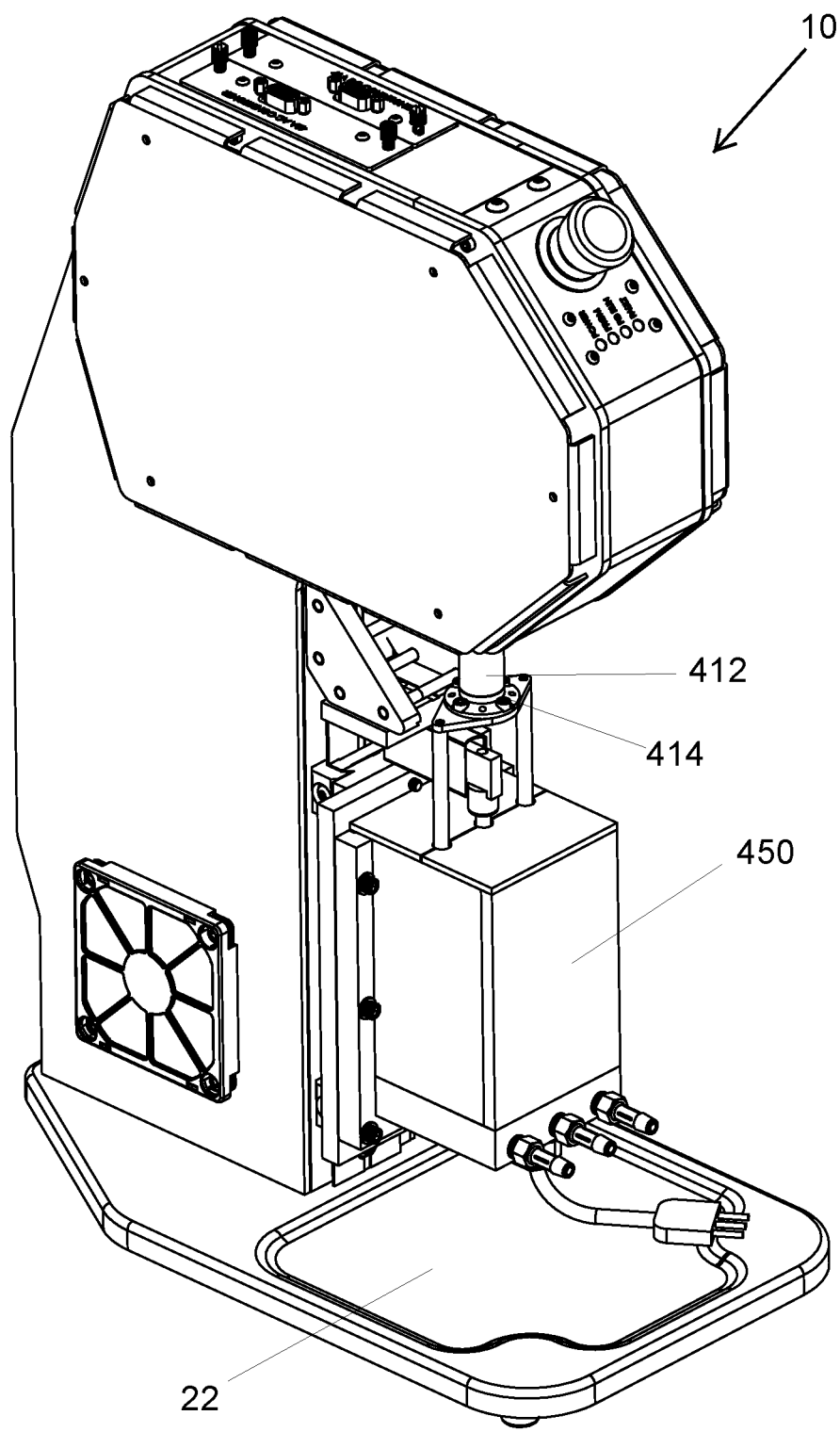
FIG. 29 is a front left top perspective view of a material testing apparatus in accordance with the present invention and having an environmental chamber mounted to the displaceable base mount of the material testing apparatus.
Figure 30:
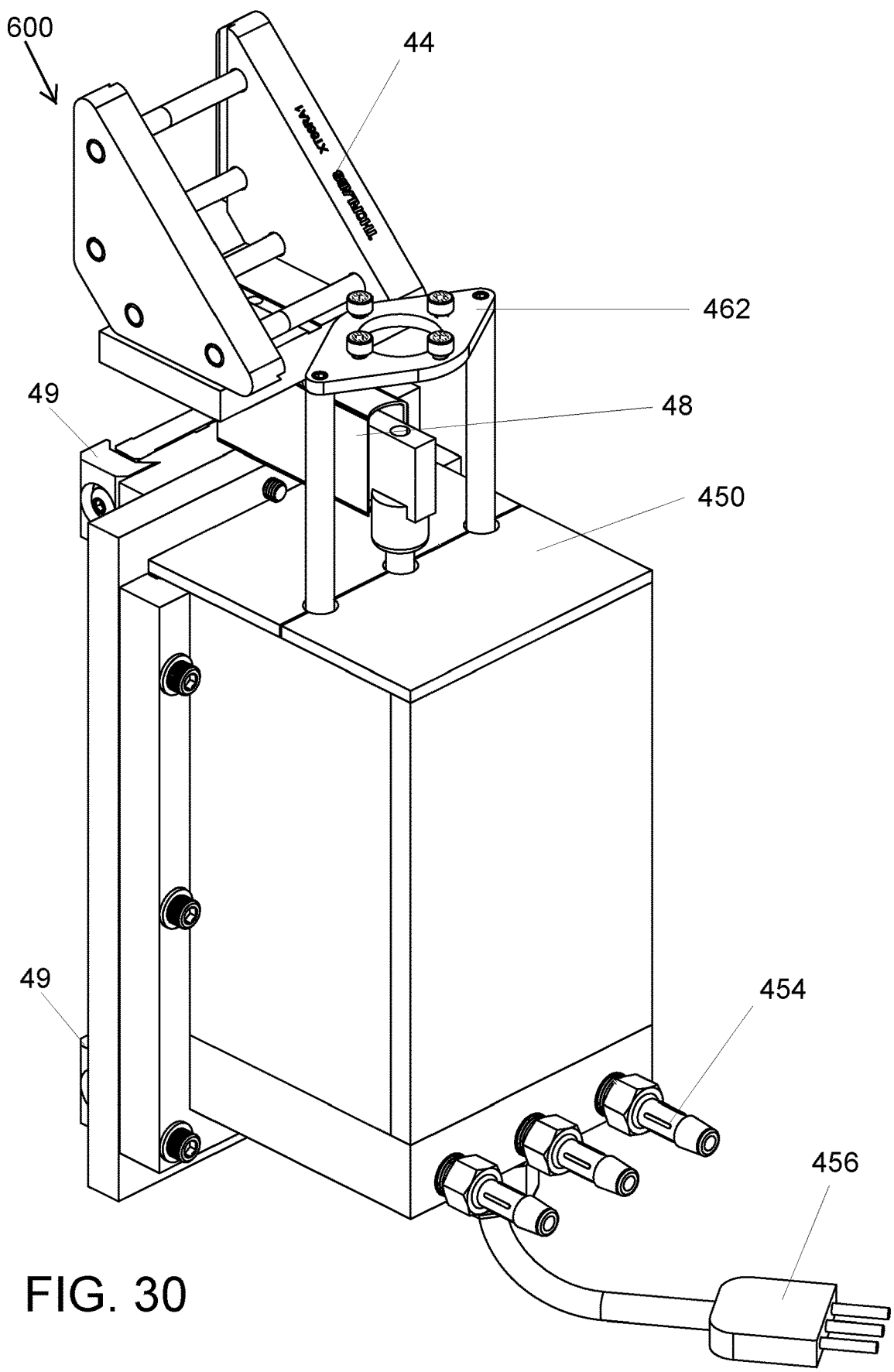
FIG. 30 is a perspective view of the environmental chamber coupled to a partial sectioned portion of the linear displacement assembly of the material testing apparatus of the present invention.
Figure 31:
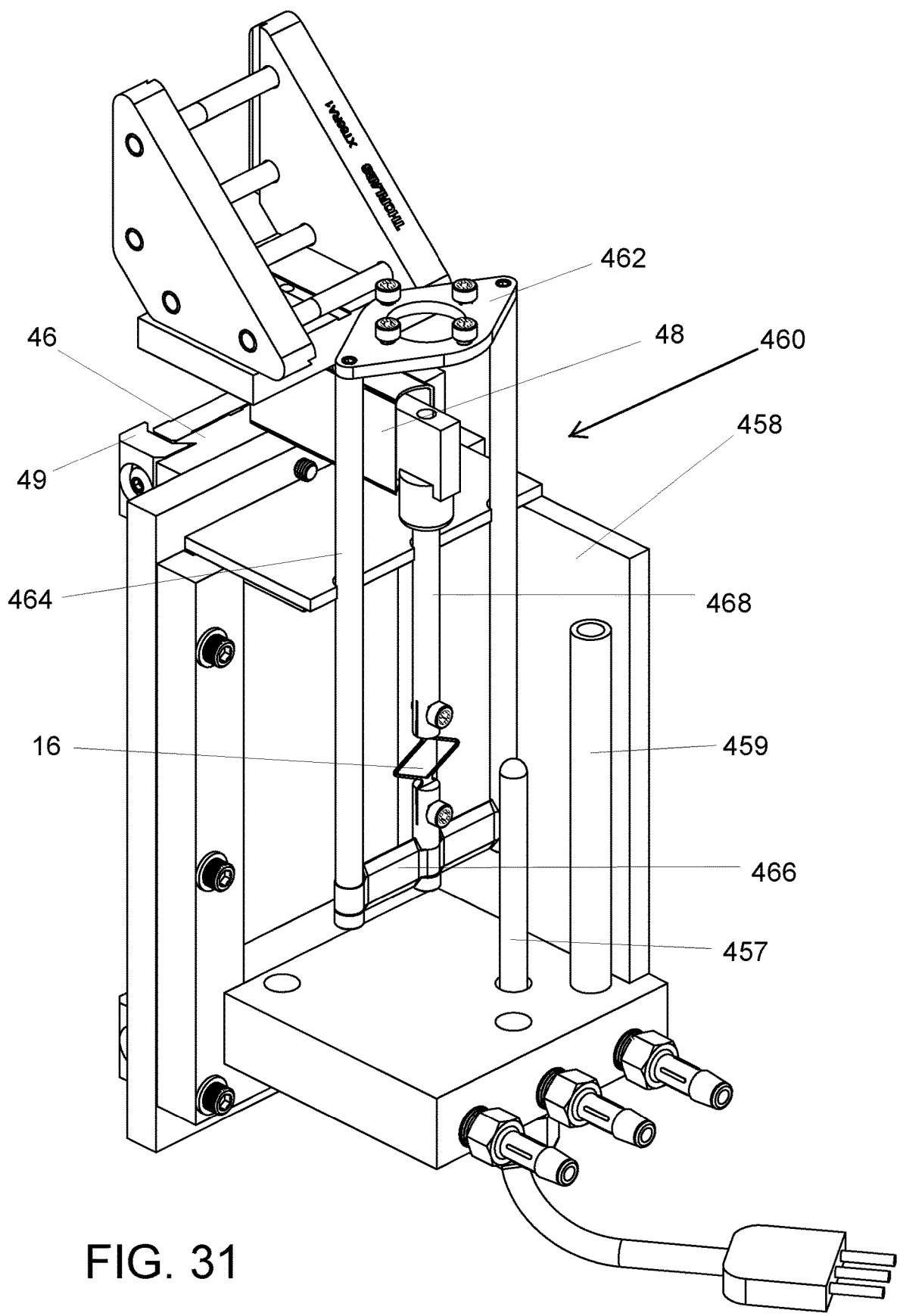
FIG. 31 is a front left partial sectioned perspective view of the environmental chamber coupled to a partial sectioned portion of the linear displacement assembly of the material testing apparatus of the present invention.
Figure 32:
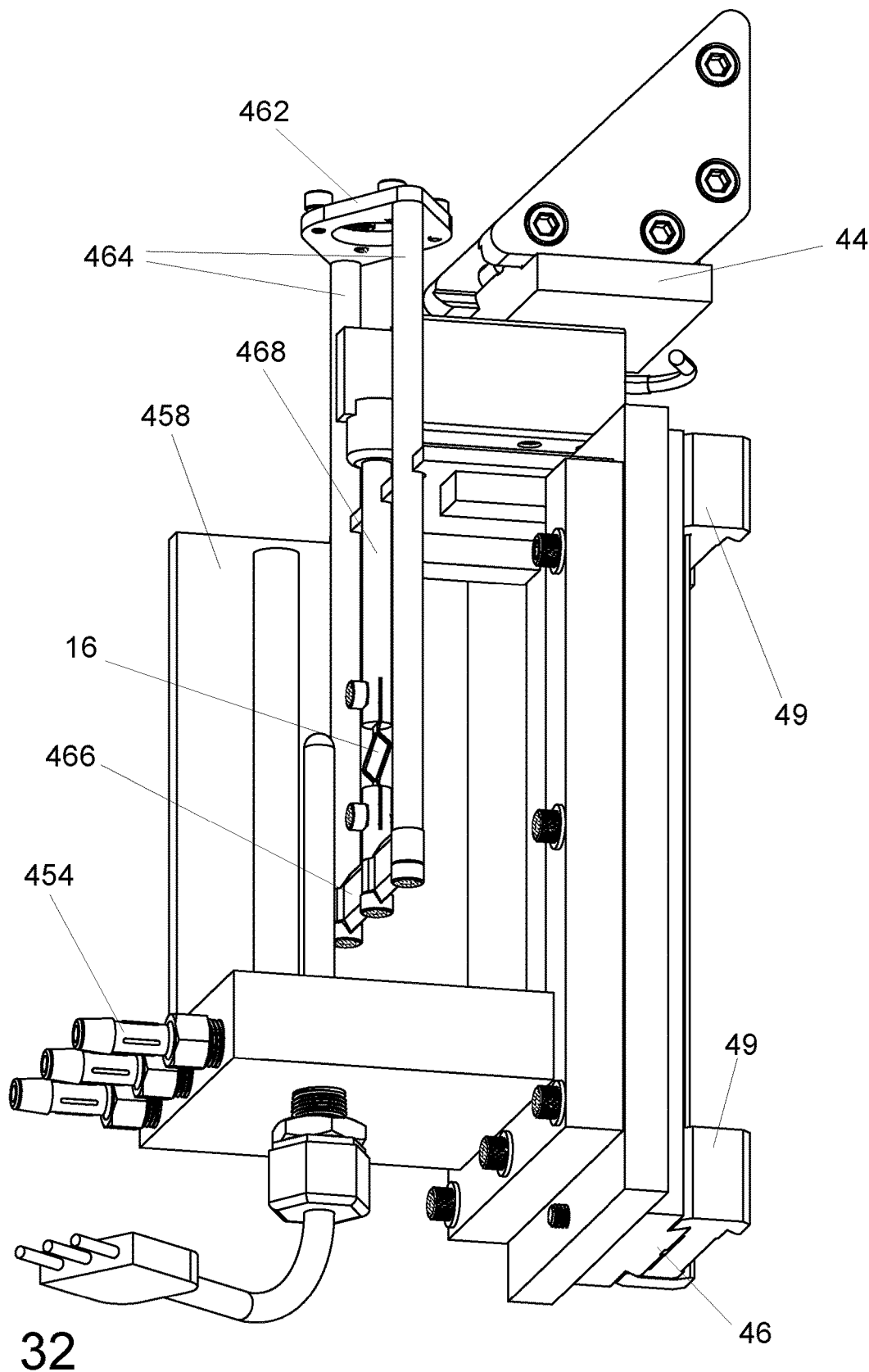
FIG. 32 is a bottom front right partial sectioned perspective view of the environmental chamber coupled to a partial sectioned portion of the linear displacement assembly of the material testing apparatus of the present invention.
Figure 33:
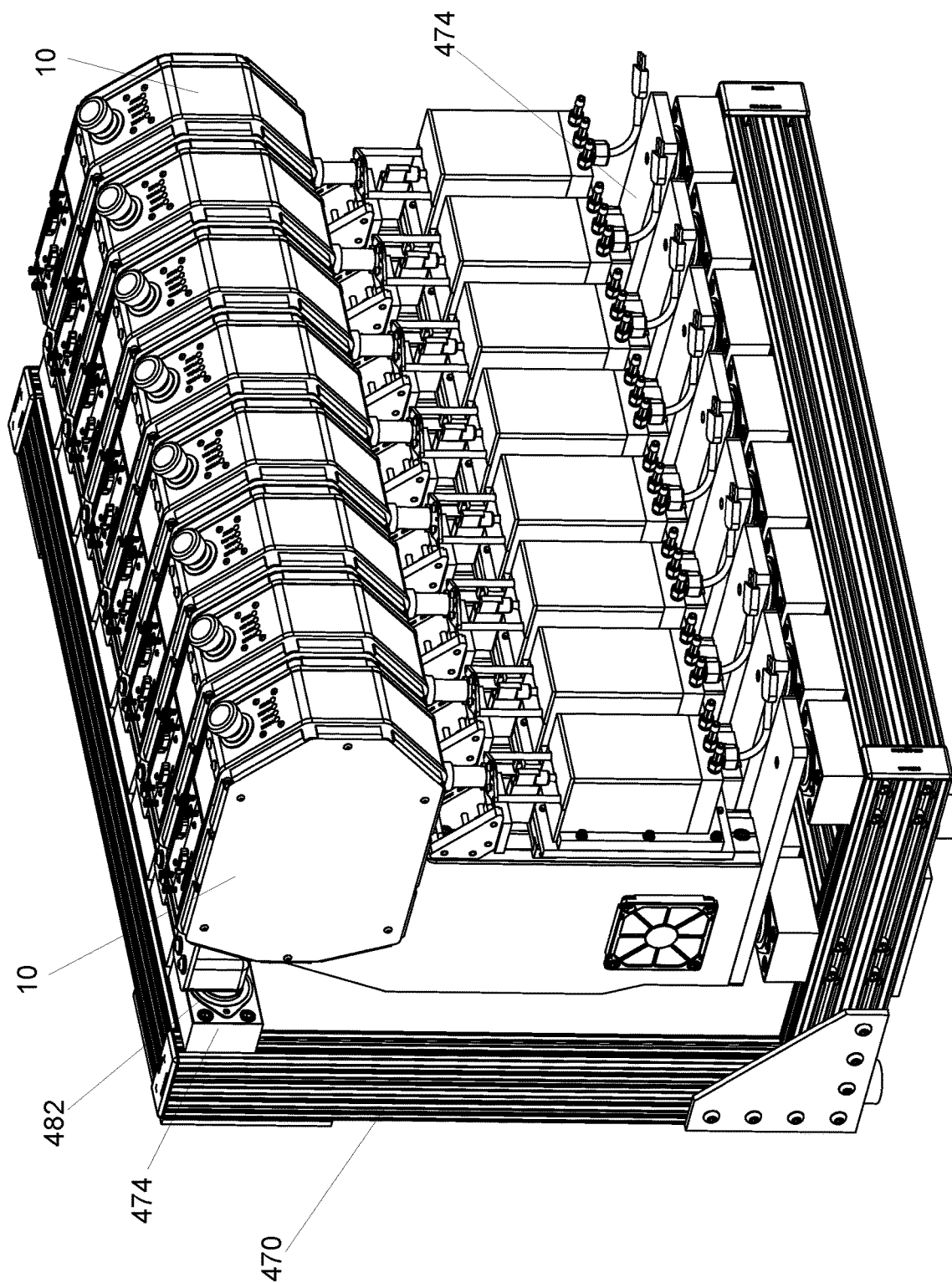
FIG. 33 is a front left top perspective view of a plurality of material testing apparatus in accordance with the present invention coupled side by side to a framework.
Figure 34:
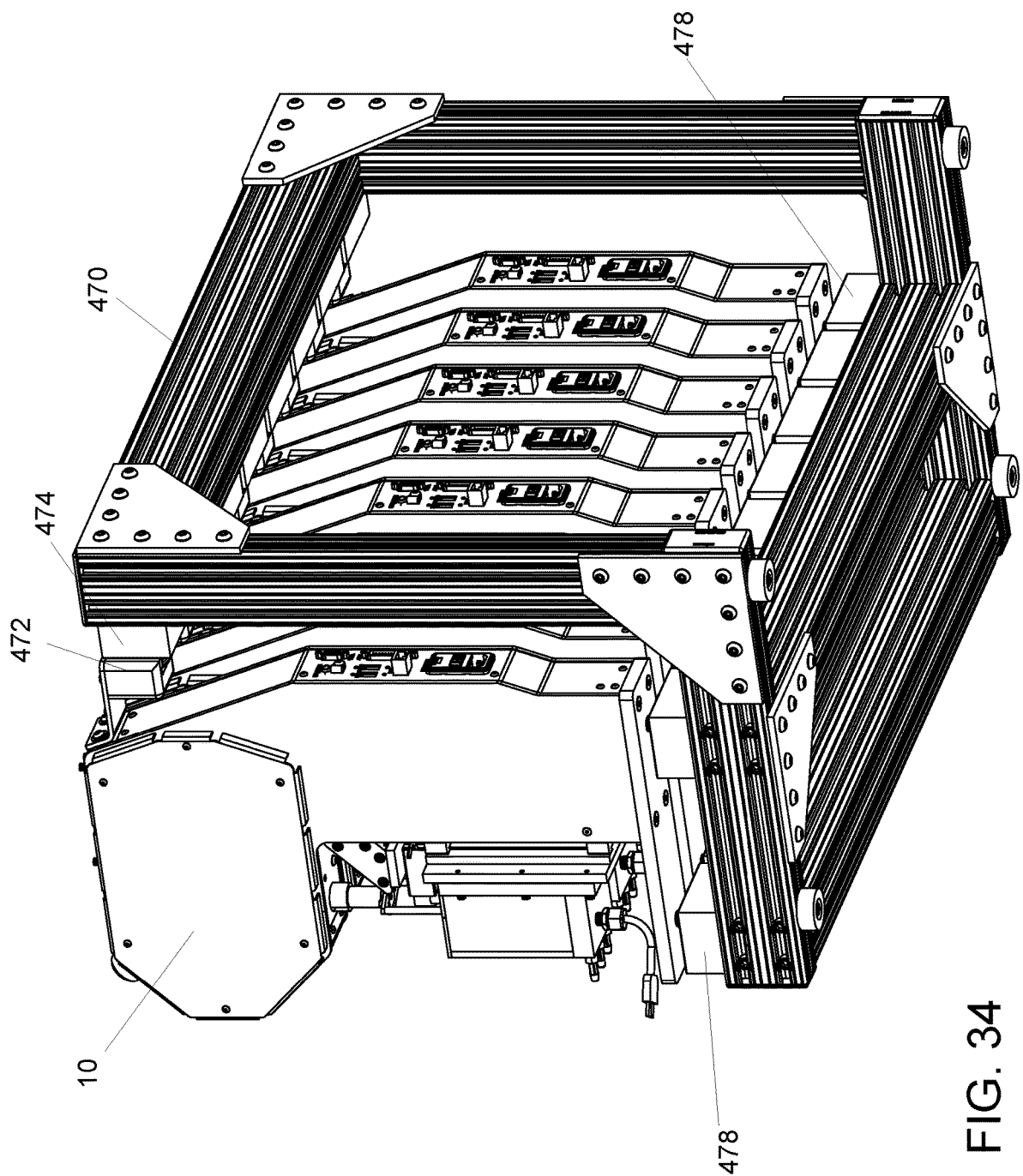
FIG. 34 is a back right bottom perspective view of a plurality of material testing apparatus in accordance with the present invention coupled side by side to a framework.
Figure 35:
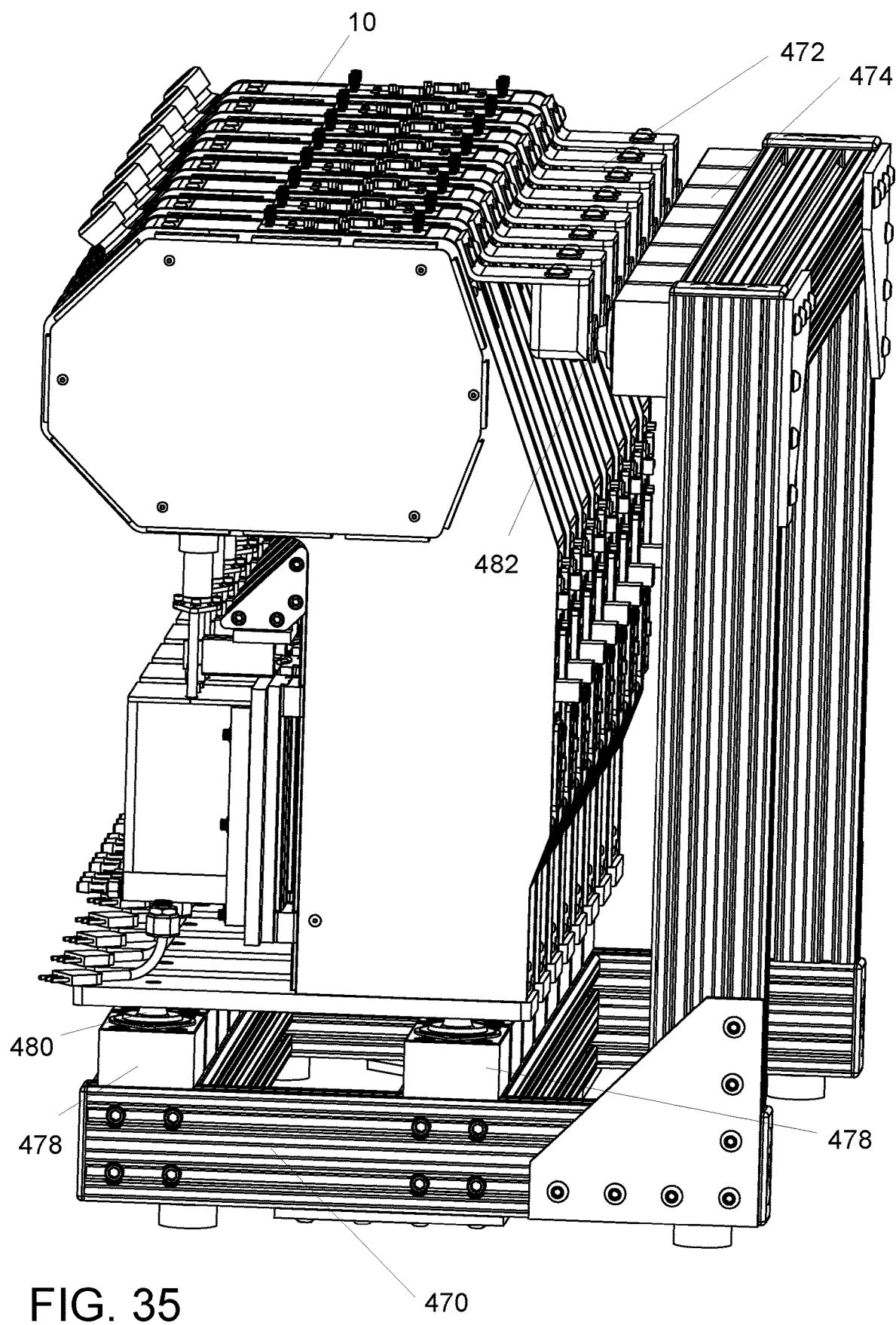
FIG. 35 is a right side perspective view of a plurality of material testing apparatus in accordance with the present invention coupled side by side to a framework.
Figure 36:
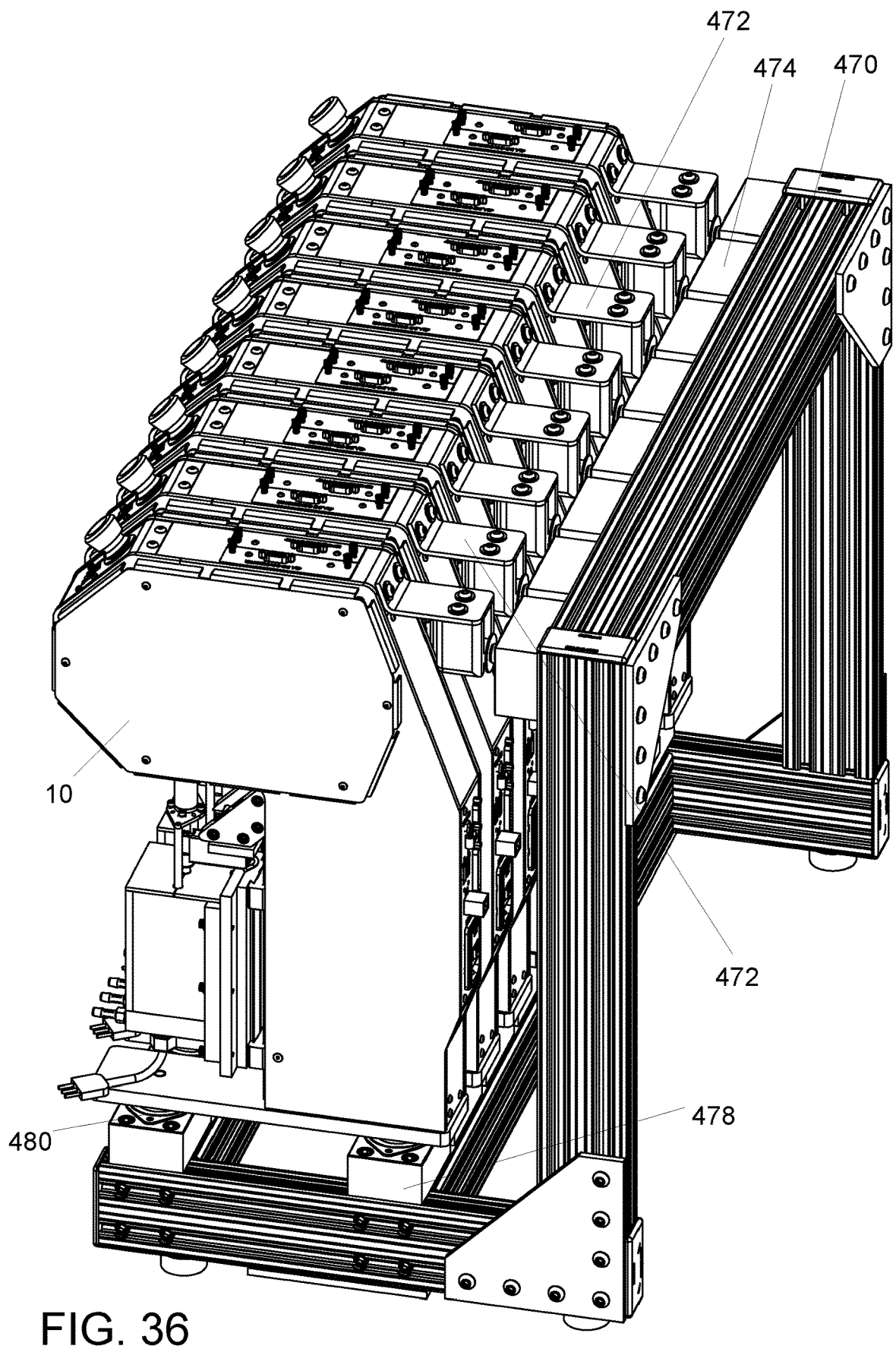
FIG. 36 is a right top side perspective view of a plurality of material testing apparatus in accordance with the present invention coupled side by side to a framework.

In certain embodiments in accordance with the present invention the linear displacement assembly may simply include a push pull tube 412 and upper grip attachment point 414 (see FIG. 26). In this manner the user may choose whether to add the LVDT assembly 430 to the displacement assembly 430 or simply operate the testing apparatus without linear displacement sensing. In this instance the load sensing assembly 600 may be included or may also be optional equipment for the user to implement.

With reference to FIGS. 28-32, an exemplary use of the material testing apparatus 10 will next be described. An environmental chamber 450 may be mounted to the column 24 using dovetail mounting plate 46 and clamps 49. The environmental chamber 450 includes an internal loading frame 460 comprised of an attachment point 462 which connects to upper grip attachment point 414, side columns 464, lower crosshead and specimen grip 466 and center column and specimen grip 468. In the configuration shown attachment point 462, side columns 464 and lower crosshead and specimen grip 466 move vertically with the linear displacement assembly 400. The center column and specimen grip 468 is mounted directly to the sensing end of load cell 48 and remains stationary.

Note that in this configuration the load sensing assembly is mounted inverted from the non-chamber configuration. The internal loading frame applies linear force or displacement from the linear displacement assembly 400 to the specimen 16 gripped between lower crosshead and specimen grip 466 and center column and specimen grips 468.

The environmental chamber top, bottom and sidewalls 458 are typically fabricated from clear material so that the specimen may be observed throughout the test. The environmental chamber is typically filled with Phosphate Buffered Saline (PBS) and includes a drain tube 459 to ensure the fluid level is maintained above the top of the specimen. Fluid interconnects 454 are provided for routing the fluid into and out of the chamber. The temperature of the PBS is maintained at a certain temperature (typically 37 degree C.) and can be controlled externally using a heated water bath or by means of a heating element located within the chamber. Temperature sensor 457 is provided for monitoring and controlling the fluid temperature.

With reference to FIGS. 33-36, at times it may be desirable to run the same or different load material fatigue or durability tests on multiple samples while simultaneously monitoring the effect of the applied cyclic load or displacement affects on the multiple samples. Replacing base 22 with lower multi-station adapter plate 476 and upper multi-station adapter 472, a plurality of material testing apparatus may be mounted to frame 470. Frame 470 includes lower attachment blocks 478 with vibration isolation mounts 480 which connect to lower multi-station adapter plate 476. Likewise, frame 470 includes upper attachment blocks 474 with vibration isolation mounts 480 which connect to upper multi-station adapter 472.

As mentioned above and in reference to FIG. 37, a single host computer 710 can link to and control multiple material testing apparatuses 10. Using a software program which runs on the host computer, the user can select the desired material test apparatus, turn it on/off, set limits, setup and run test waveforms, and gather, display and store data generated by the material test apparatus.

These and various other aspects and features of the invention are described with the intent to be illustrative, and not restrictive. This invention has been described herein with detail in order to comply with the patent statutes and to provide those skilled in the art with information needed to apply the novel principles and to construct and use such specialized components as are required. It is to be understood, however, that the invention can be carried out by specifically different constructions, and that various modifications, both as to the construction and operating procedures, can be accomplished without departing from the scope of the invention. Further, in the appended claims, the transitional terms comprising and including are used in the open ended sense in that elements in addition to those enumerated may also be present. Other examples will be apparent to those of skill in the art upon reviewing this document.

What is claimed is:

1. A material testing apparatus having vibration mitigation, the apparatus comprising:
   a support framework;
   a stator coupled to the support framework;
   a first armature having a cross-flexure assembly, arms, and a first set of permanent magnets, wherein a first end of the arms of the first armature are coupled to the cross-flexure assembly of the first armature and a free end of the arms of the first armature have the first set of permanent magnets affixed thereto, wherein a portion of the cross-flexure assembly of the first armature is fixed to the support framework and another portion of the cross-flexure assembly of the first armature is mounted to the arms of the first armature to allow the first armature to pivot;
   a second armature having a cross-flexure assembly, arms, and a second set of permanent magnets, wherein a first end of the arms of the second armature are coupled to the cross-flexure assembly of the second armature and a free end of the arms of the second armature have the second set of permanent magnets affixed thereto, wherein a portion of the cross-flexure assembly of the second armature is fixed to the support framework and another portion of the cross-flexure assembly of the second armature is mounted to the arms of the second armature to allow the second armature to pivot;
   an interconnection flexure connecting the cross-flexure assembly of the first armature with the cross-flexure assembly of the second armature;
   a linear displacement assembly;
   a displacement flexure coupling the second armature to the linear displacement assembly; and
   a displaceable base coupled to the support framework below the linear displacement assembly.

2. The apparatus as recited in claim 1, wherein the portion of the cross-flexure assembly of the first armature that is fixed to the support framework is spaced apart from the portion of the cross-flexure assembly of the second armature that is fixed to the support framework such that the free end of the arms of the first armature and the free end of the arms of the second armature move in opposing directions thereby cancelling vibrations from movement of the first and second armatures.

3. The apparatus as recited in claim 2, wherein movement of the first and second armatures provides an additive force against the linear displacement assembly.

4. The apparatus as recited in claim 1, wherein the stator includes first and second spaced apart c-shaped cores oriented such that ends of the first and second c-shaped cores are aligned but opposed to form a first gap and a second gap between respective opposing ends of the first and second c-shaped cores.

5. The apparatus as recited in claim 4, wherein each end of each of the first and second c-shaped cores includes a coil surrounding an end portion of the end.

6. The apparatus as recited in claim 5, wherein the first set of permanent magnets are positioned within the first gap and the second set of permanent magnets are positioned in the second gap.

7. The apparatus as recited in claim 1, wherein the cross-flexure assembly of the second armature includes two flexures and each of the two flexures includes at least one strain gage coupled thereto.

8. The apparatus as recited in claim 1, further including an environmental chamber mounted to the displaceable base.

9. The apparatus as recited in claim 1, wherein the linear displacement assembly includes displacement sensing and wherein the apparatus further includes a micro controller to control and monitor linear displacement of the linear displacement assembly.

10. The apparatus as recited in claim 1, wherein the displaceable base includes a load sensing assembly and wherein the apparatus further includes a micro controller to control and monitor at least one of linear displacement of the linear displacement assembly and a load applied to a specimen.

11. The apparatus as recited in claim 10, wherein the load sensing assembly includes a means for increasing a critical damping ratio of the load sensing assembly so that at accelerated test frequencies the load sensing assembly does not overstate an applied load.

12. The apparatus as recited in claim 1, further including a frame suitable for coupling a plurality of the apparatus thereto.

13. The apparatus as recited in claim 1, further including a plurality of the apparatus each of which is coupled to a host computer.

14. A material testing apparatus having vibration mitigation, the apparatus comprising:
a support framework;
a stator coupled to the support framework, wherein the stator includes first and second spaced apart c-shaped cores oriented such that ends of the first and second c-shaped cores are aligned but opposed to form a first gap and a second gap between opposing ends of the first and second c-shaped cores, and further wherein each end of each of the first and second c-shaped cores includes a coil surrounding an end portion of each end;
a first armature having a cross-flexure assembly, arms, and a first set of permanent magnets, wherein a first end of the arms of the first armature are coupled to the cross-flexure assembly of the first armature and a free end of the arms of the first armature have the first set of permanent magnets affixed thereto, wherein a portion of the cross-flexure assembly of the first armature is fixed to the support framework and another portion of the cross-flexure assembly of the first armature is mounted to the arms of the first armature to allow the first armature to pivot;
a second armature having a cross-flexure assembly, arms, and a second set of permanent magnets, wherein a first end of the arms of the second armature are coupled to the cross-flexure assembly of the second armature and a free end of the arms of the second armature have the second set of permanent magnets affixed thereto, wherein a portion of the cross-flexure assembly of the second armature is fixed to the support framework and another portion of the cross-flexure assembly of the second armature is mounted to the arms of the second armature to allow the second armature to pivot;
an interconnection flexure connecting the cross-flexure assembly of the first armature with the cross-flexure assembly of the second armature;
a linear displacement assembly;
a displacement flexure coupling the second armature to the linear displacement assembly; a displaceable base mount coupled to the support framework below the linear displacement assembly; and
wherein the first set of permanent magnets are positioned within the first gap of the stator and the second set of permanent magnets are positioned in the second gap of the stator.

15. The apparatus as recited in claim 14, wherein the portion of the cross-flexure assembly of the first armature that is fixed to the support framework is spaced apart from the portion of the cross-flexure assembly of the second armature that is fixed to the support framework such that the free end of the arms of the first armature and the free end of the arms of the second armature move in opposing directions thereby cancelling vibrations from movement of the first and second armatures.

16. The apparatus as recited in claim 14, wherein movement of the first and second armatures provides an additive force against the linear displacement assembly.

17. The apparatus as recited in claim 14, wherein the cross-flexure assembly of the second armature includes two flexures and each of the two flexures includes at least one strain gage coupled thereto.

18. The apparatus as recited in claim 14, further including an environmental chamber mounted to the displaceable base mount.

19. The apparatus as recited in claim 14, wherein the linear displacement assembly includes displacement sensing and wherein the apparatus further includes a micro controller to control and monitor linear displacement of the linear displacement assembly.

20. The apparatus as recited in claim 14, further including a micro controller to control and monitor linear displacement of the linear displacement assembly.

21. The apparatus as recited in claim 14, wherein the displaceable base includes a load sensing assembly.

22. The apparatus as recited in claim 14, further including a frame suitable for supporting a plurality of the apparatus and a host computer coupled to the plurality of the apparatus.

23. The apparatus as recited in claim 14, wherein the displaceable base includes a load sensing assembly and wherein the apparatus further includes a micro controller to control and monitor at least one of linear displacement of the linear displacement assembly and a load applied to a specimen.

24. The apparatus as recited in claim 23, wherein the load sensing assembly includes a means for increasing a critical damping ratio of the load sensing assembly so that at accelerated test frequencies the load sensing assembly does not overstate an applied load.

* * * * *